(12) United States Patent
Haass-Koffler

(10) Patent No.: US 11,278,527 B2
(45) Date of Patent: Mar. 22, 2022

(54) COMPOSITIONS AND METHODS FOR THE MODULATION OF THE CORTICOTROPIN RELEASING FACTOR BINDING PROTEIN AND THE TREATMENT OF ALCOHOL USE DISORDER

(71) Applicant: Brown University, Providence, RI (US)

(72) Inventor: Carolina L. Haass-Koffler, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

(21) Appl. No.: 17/273,607

(22) PCT Filed: Sep. 4, 2019

(86) PCT No.: PCT/US2019/049498
§ 371 (c)(1),
(2) Date: Mar. 4, 2021

(87) PCT Pub. No.: WO2020/051206
PCT Pub. Date: Mar. 12, 2020

(65) Prior Publication Data
US 2021/0308107 A1    Oct. 7, 2021

Related U.S. Application Data

(60) Provisional application No. 62/726,830, filed on Sep. 4, 2018.

(51) Int. Cl.
*A61K 31/4245* (2006.01)
*A61K 31/517* (2006.01)

(52) U.S. Cl.
CPC ........ *A61K 31/4245* (2013.01); *A61K 31/517* (2013.01)

(58) Field of Classification Search
CPC ... A61K 31/4245; A61K 31/517; A61P 25/30; A61P 25/32
See application file for complete search history.

(56) References Cited

U.S. PATENT DOCUMENTS

2016/0354375 A1   12/2016   Sheridan et al.

FOREIGN PATENT DOCUMENTS

| WO | 2013169631 A2 | 11/2013 |
|---|---|---|
| WO | 2014176460 A1 | 10/2014 |

OTHER PUBLICATIONS

Quadros et al. Frontiers in Endocrinology, 2016, vol. 7, article 134, 25 pages (Year: 2016).*

Haass-Koffler, CL et al. "Defining the role of corticotropin releasing factor binding protein in alcohol consumption." Translational Psychiatry, vol. 6, 2016, e953, pp. 1-9.
Khattak, MNK et al. "CRH and SRIF Have Opposite Effects on the Wnt/beta-Catenin Signalling Pathway Through PKA/GSK-3 beta in Corticotroph Pituitary Cells." Cancer Investigation, vol. 28, 2010, pp. 797-805.
Parker, JG et al. "The Contribution of NMDA Receptor Signaling in the Corticobasal Ganglia Reward Network to Appetitive Pavlovian Learning." The Journal of Neuroscience, vol. 31, No. 31, Aug. 3, 2011, pp. 11362-11369.
PUBCHEM. 2-(2-Bromophenyl)-5-[(1-phenyltetrazol-5-yl)sulfanylmethyl]-1,3,4-oxadiazole. Jul. 16, 2005, pp. 1-8 [online]. [retrieved on Oct. 17, 2019]. Retrieved from the Internet <URL:https://pubchem.ncbi.nlm.nih. govcompound/2621181>; p. 2.
PUBCHEM. MLS-0219419.0001. Oct. 17, 2012, pp. 1-4 [online], [retrieved on Oct. 17, 2019]. Retrieved from the Internet <URL:https://pubchem.ncbi.nlm.nih.gov/substance/144241312>; p. 2.
International Search Report and Written Opinion of PCT/US2019/049498 dated Nov. 12, 2019; 12 pgs.
Addolorato et al., "Baclofen in the Treatment of Alcohol Withdrawal Syndrome: A Comparative Study vs Diazepam", The American Journal of Medicine, vol. 119, No. 3, pp. 276.e13-276 e 18, Mar. 2006.
Albrechet-Souza et al., "CRF Binding Protein and CRF2 Receptors in the Ventral Tegmental Area: Modulation of Ethanol Binge Drinking in C57BL/6J Mice", Alcoholism, clinical and experimental research, vol. 39, No. 9, pp. 1609-1618, Sep. 2015.

(Continued)

*Primary Examiner* — James D. Anderson
(74) *Attorney, Agent, or Firm* — Adler Pollock & Sheehan P.C.; Michel Morency

(57) ABSTRACT

Stress responses involve corticotropin releasing factor (CRF), the two cognate receptors ($CRF_1$ and $CRF_2$) and the CRF-binding protein (CRFBP). Utilizing a novel cell-based assay, a C-terminal CRFBP fragment [CRFBP(10 kD)] was found to potentiates CRF-intracellular $Ca^{2+}$ release, demonstrating that CRFBP possesses excitatory roles in addition to the inhibitory role established by the N-terminal fragment of CRFBP [CRFBP(27 kD)]. This interaction was $CRF_2$-specific, as $CRF_1$ responses were not potentiated by CRFBP (10 kD). As there were currently no small molecule ligands available that selectively interact with either CRFBP or $CRF_2$, a cell-based assay was miniaturized, wherein CRFBP (10 kD) was fused as a chimera with $CRF_{2\alpha}$, that allowed us to a perform a high-throughput screen (HTS) of approximately 350,000 small molecules. This resulted in the identification of negative allosteric modulators (NAMs) of the CRFBP(10 kD)-$CRF_2$ complex that blunt CRF-induced potentiation of N-Methyl-D-aspartic acid receptor (NMDAR)-mediated synaptic transmission in dopamine neurons in the ventral tegmental area (VTA). These results provide the first evidence of specific roles for $CRF_2$ and CRFBP in the modulation of neuronal activity and suggest that NMDARs in the VTA may be a target for the treatment of stress and substance abuse disorders such as alcohol use disorder.

4 Claims, 9 Drawing Sheets

(56) References Cited

OTHER PUBLICATIONS

Bechtholt et al., "Ethanol-induced Conditioned Place Preference Is Expressed Through a Ventral Tegmental Area Dependent Mechanism", Behavioral neuroscience, vol. 119, No. 1, pp. 213-223, Feb. 2005 (English Abstract Submitted).
Behan et al., "Corticotropin Releasing Factor (CRF) Binding Protein: a Novel Regulator of CRF and Related Peptides", Front Neuroendocrinol, vol. 16, No. 4, pp. 362-382, Oct. 1995 (English Abstract Submitted).
Bernier et al., "Previous Ethanol Experience Enhances Synaptic Plasticity of NMDA Receptors in the Ventral Tegmental Area", The Journal of Neuroscience, vol. 31, No. 14, pp. 5205-5212, Apr. 6, 2011.
Brodie et al., "Ethanol Increases the Firing Rate of Dopamine Neurons of the Rat Ventral Tegmental Area in Vitro", Brain research, vol. 508, No. 1, pp. 65-90, Jan. 29, 1990 (English Abstract Submitted).
Christopoulos et al., "G Protein-Coupled Receptor Allosterism and Complexing", Pharmacological Reviews, vol. 54, No. 2, pp. 323-374, Jun. 2002 (English Abstract Submitted).
Donoghue et al., "The Efficacy of Acamprosate and Naltrexone in the Treatment of Alcohol Dependence, Europe Versus the Rest of the World: A Meta-analysis", Addiction, vol. 110, No. 6, pp. 920-930, 2015.
Garbutt, James C., "Efficacy and Tolerability of Naltrexone in the Management of Alcohol Dependence", Current Pharmaceutical Design, vol. 16, pp. 2091-2097, 2010.
Gatto et al., "Ethanol Self-infusion Into the Ventral Tegmental Area by Alcohol-preferring Rats", Alcohol, vol. 11, Issue 6, pp. 557-564, Nov.-Dec. 1994 (English Abstract Submitted).
Gehlert et al., "3-(4-Chloro-2-Morpholin-4-yl-Thiazol-5-yl)-8-(1-Ethylpropyl)-2,6-Dimethyl-Imidazo[1,2-b]Pyridazine: A Novel Brain-Penetrant, Orally Available Corticotropin-Releasing Factor Receptor 1 Antagonist with Efficacy in Animal Models of Alcoholism", The Journal of Neuroscience, vol. 27, Issue 10, pp. 2718-2726, Mar. 7, 2007.
Gehlert et al., "Effects of Corticotropin-releasing Factor 1 Receptor Antagonism on the Hypothalamic-pituitary-adrenal Axis of Rodents", Journal of Pharmacology and Experimental Therapeutics, vol. 341, No. 3, pp. 672-680, Jun. 2012 (English Abstract Submitted).
George et al., "Addiction as a Stress Surfeit Disorder", Neuropharmacology, vol. 76, Issue 0, pp. 370-382, Jan. 2014.
Goh et al., "Review Article: Pharmacotherapy for Alcohol Dependence: the Why, the What and the Wherefore", Alimentary pharmacology & therapeutics, vol. 45, Issue 7, pp. 865-882, Feb. 21, 2017.
Haass-Koffler et al., "Altering Ethanol Pharmacokinetics to Treat Alcohol Use Disorder: Can You Teach an Old Dog New Tricks?", J Psychopharmacol, vol. 31, Issue 7, pp. 812-818, Jul. 2017.
Haass-Koffler et al., "An Analytical Tool That Quantifies Cellular Morphology Changes From Three-dimensional Fluorescence Images", Journal of Visualized Experiments, vol. 66, No. e4233, pp. 1-6, Aug. 31, 2012.
Haass-Koffler et al., "Pharmacological Approaches to Reducing Craving in Patients with Alcohol Use Disorders", CNS Drugs, vol. 28, Issue 4, pp. 343-360, Apr. 2014.
Haass-Koffler, Carolina L, "Role of Corticotropin Releasing Factor Binding Protein in the Stress System: a Strange Case of Dr. Jekyll and Mr. Hyde in the Stress System?", Alcohol, vol. 72, pp. 3-8, Nov. 2018.
Haass-Koffler et al., "Stress and Addiction: Contribution of the Corticotropin Releasing Factor (CRF) System in Neuroplasticity", Frontiers in molecular neuroscience, vol. 5, Article 91, pp. 1-13, Sep. 6, 2012.
Higley et al., "Treatment of Alcohol Dependence With Drug Antagonists of the Stress Response", Alcohol Research, vol. 34, Issue 4, pp. 516-521, 2012.

Hodge et al., "Ventral Tegmental Microinjections of Quinpirole Decrease Ethanol and Sucrose-reinforced Responding", Alcoholism, clinical and experimental research, vol. 17, No. 2, pp. 370-375, Apr. 1993 (English Abstract Submitted).
Hopf et al., "Withdrawal From Intermittent Ethanol Exposure Increases Probability of Burst Firing in VTA Neurons In Vitro", Journal of neurophysiology, vol. 98, pp. 2297-2310, Aug. 15, 2007.
Jonas et al., "Pharmacotherapy for Adults With Alcohol Use Disorders in Outpatient Settings: A Systematic Review and Meta-analysis", JAMA, vol. 311, Issue 18, pp. 1889-1900, May 14, 2014.
Leggio et al., "New Developments for the Pharmacological Treatment of Alcohol Withdrawal Syndrome. A Focus on Non-benzodiazepine Gabaergic Medications", Prog Neuropsychopharmacol Biol Psychiatry, vol. 32, No. 5, pp. 1106-1117, Jul. 1, 2008 (English Abstract Submitted).
Lejoyeux et al., "Benzodiazepine Treatment for Alcohol-dependent Patients", Alcohol & Alcoholism vol. 33, No. 6, pp. 563-575, Nov.-Dec. 1998.
Lowry et al., "Nature of Ligand Affinity and Dimerization of Corticotrophin-releasing Factor-binding Protein May Be Detected by Circular Dichroism", Journal of Molecular Endocrinology, vol. 16, No. 1, pp. 39-44, Feb. 1996 (English Abstract Submitted).
Nowak et al., "Involvement of Dopamine D2 Autoreceptors in the Ventral Tegmental Area on Alcohol and Saccharin Intake of the Alcohol-preferring P Rat", Alcoholism, clinical and experimental research, vol. 24, No. 4, pp. 476-483, Apr. 2000 (English Abstract Submitted).
Pignatelli et al., "Synaptic Plasticity Onto Dopamine Neurons Shapes Fear Learning", Neuron, vol. 93, pp. 425-440, Jan. 18, 2017.
Plosker, Greg L., "Acamprosate: A Review of Its Use in Alcohol Dependence", Drugs, vol. 75, No. 11, pp. 1255-1268, Jun. 18, 2015 (English Abstract Submitted).
Potter et al., "The Central Distribution of a Corticotropin-releasing Factor (CRF)-binding Protein Predicts Multiple Sites and Modes of Interaction With CRF", Neurobiology, Proceedings of the National Academy of Sciences of the United States of America, vol. 89, pp. 4192-4196, May 1992.
Qatari et al., "Mechanism of Action of Acamprosate. Part Ii. Ethanol Dependence Modifies Effects of Acamprosate on NMDA Receptor Binding in Membranes From Rat Cerebral Cortex", Alcoholism, clinical and experimental research, vol. 22, No. 4, pp. 810-814, Jun. 1998 (English Abstract Submitted).
Rodd et al., "Intracranial Self-Administration of Ethanol within the Ventral Tegmental Area of Male Wistar Rats: Evidence for Involvement of Dopamine Neurons", The Journal of Neuroscience, vol. 24, Issue 5, pp. 1050-1057, Feb. 4, 2004.
Slater et al., "Corticotropin-releasing Factor Type-2 Receptor and Corticotropin-releasing Factor-binding Protein Coexist in Rat Ventral Tegmental Area Nerve Terminals Originated in the Lateral Hypothalamic Area", The European journal of neuroscience, vol. 43, No. 2, 220-229, Nov. 28, 2015 (English Abstract Submitted).
Slater et al., "CRF Binding Protein Facilitates the Presence of Crf Type 2α Receptor on the Cell Surface", Proceedings of the National Academy of Sciences, vol. 113, No. 15, pp. 4075-4080, Apr. 12, 2016.
Slater et al., "Molecular Modeling of Structures and Interaction of Human Corticotropin-releasing Factor (CRF) Binding Protein and CRF Type-2 Receptor", Frontiers in Endocrinology, vol. 9, Article 43, 14 Pages, Feb. 20, 2018.
Sombers et al., "Synaptic Overflow of Dopamine in the Nucleus Accumbens Arises from Neuronal Activity in the Ventral Tegmental Area", The Journal of Neuroscience, vol. 29, Issue 6, pp. 1735-1742, Feb. 11, 2009.
Sparta et al., "Binge Ethanol Drinking Potentiates Corticotropin Releasing Factor R1 Receptor Activity in the Ventral Tegmental Area", Alcoholism, clinical and experimental research, vol. 37, No. 10, pp. 1680-1687, Oct. 2013.
Spierling et al., "Don't Stress About CRF: Assessing the Translational Failures of Crf1 Antagonists", Psychopharmacology (Berl), vol. 234, Issue 9-10, pp. 1467-1481, May 2017.
Srisurapanont et al., "Opioid Antagonists for Alcohol Dependence", The Cochrane database of systematic reviews, vol. 3, 2 pages, 2000 (English Abstract Submitted).

(56) References Cited

OTHER PUBLICATIONS

Ungless et al., "Corticotropin-Releasing Factor Requires CRF Binding Protein to Potentiate NMDA Receptors via CRF Receptor 2 in Dopamine Neurons", Neuron, vol. 39, pp. 401-407, Jul. 31, 2003.
Wanat et al., "Corticotropin-releasing Factor Increases Mouse Ventral Tegmental Area Dopamine Neuron Firing Through a Protein Kinase C-dependent Enhancement of Ih", The Journal of physiology, vol. 568, No. 8, pp. 2157-2170, 2008.
Wang et al., "Stress-induced Relapse to Cocaine Seeking: Roles for the CRF2 Receptor and CRF-binding Protein in the Ventral Tegmental Area of the Rat", Psychopharmacology, vol. 193, pp. 283-294, Sep. 2007.
Woods et al., "Cleavage of Recombinant Human CorticotropinReleasing Factor (CRF)-Binding Protein Produces a 27-Kilodalton Fragment Capable of Binding CRF", The Journal of clinical endocrinology and metabolism, vol. 84, No. 8, pp. 2788-2794, Aug. 1999.
Zellner et al., "NMDA Receptor Antagonism in the Ventral Tegmental Area Impairs Acquisition of Reward-related Learning", Behavioural Brain Research, vol. 197, Issue 2, pp. 442-449, Feb. 11, 2009 (English Abstract Submitted).
Zweifel et al., "Disruption of NMDAR-dependent Burst Firing by Dopamine Neurons Provides Selective Assessment of Phasic Dopamine-dependent Behavior", Proceedings of the National Academy of Sciences, vol. 106, No. 18, pp. 7281-7288, May 5, 2009.

\* cited by examiner

A  B

MLS-0046818  MLS-0219419

COMPOSITIONS AND METHODS FOR THE MODULATION OF THE CORTICOTROPIN RELEASING FACTOR BINDING PROTEIN AND THE TREATMENT OF ALCOHOL USE DISORDER

CROSS REFERENCE TO RELATED APPLICATIONS

This application is a national phase filing under 35 U.S.C. § 371 of International Application No. PCT/US2019/049498 filed Sep. 4, 2019, which claims priority from U.S. Provisional Patent Application No. 62/726,830 filed Sep. 4, 2018, the entire contents of which are hereby incorporated by reference herein.

STATEMENT REGARDING FEDERALLY SPONSORED RESEARCH OR DEVELOPMENT

This invention was made with government support under grant number R01 AA026589 awarded by the National Institutes of Health. The government has certain rights in the invention.

FIELD OF THE INVENTION

The embodiments of the present invention generally relates to methods of using negative allosteric modulators (NAMs) of the corticotropin releasing factor binding protein (CRFBP) tethered to the G protein-coupled receptors (GPCRs) $CRF_2$ (CRFBP-$CRF_2$ complex) to modulate corticotropin releasing factor (CRF) signaling. The embodiments of the present invention also relate to methods of using NAMs for the treatment of alcohol use disorder (AUD).

BACKGROUND OF THE INVENTION

Alcohol use disorder (AUD) is a medical diagnosis given to individuals with severe problematic drinking of alcohol. To be diagnosed with an AUD in the United States, individuals must meet certain criteria outlined in the Diagnostic and Statistical Manual of Mental Disorders (DSM). For example, under the fifth edition (DSM-5), any individual meeting two of the eleven criteria during the same 12-month period receives a diagnosis of AUD. The severity of an AUD-mild, moderate, or severe, is based on the number of criteria met. In Europe, individuals are screened using the Alcohol Use Disorders Identification Test (AUDIT). People with AUD drink to excess and, consequently, can endanger both themselves and others.

AUD continues to be a significant medical and social problem. According to the 2015 National Survey on Drug Use and Health (NSDUH), 15.1 million adults age 18 and older in the United States suffer from AUD.[1] In addition, alcohol is the fourth leading preventable cause of death in the US with approximately 88,000 deaths annually.[2] Currently available treatments for AUD include detoxification, psychological counseling, behavioral therapies and the pharmacotherapies approved by the Food and Drug Administration disulfiram, naltrexone, and acamprosate.[3] Disulfiram alters ethanol metabolism and enforces abstinence by producing aversive effects after concurrent consumption of alcohol,[4] but clinical trials have generated conflicting results and a recent meta-analysis does not support its efficacy for AUD patients.[5] Conversely, naltrexone is an opioid receptor antagonist that helps block alcohol induced euphoria. While naltrexone decreases the amount and frequency of drinking,[6] only modest effects on return to drinking and abstinence are observed.[3,7,8] The mechanism of action of acamprosate is not entirely defined,[9] and has provided modest improvements in alcohol-consumption outcomes.[10] Thus, of the pharmacotherapies for AUD, clinical performance is marginal, and all the standard medications suffer from limiting contraindications.[3]

Accordingly, there remains a critical unmet need to develop more effective therapeutics for the treatment of AUD.

BRIEF SUMMARY OF THE INVENTION

The embodiments of the present invention provide compositions and methods for the treatment of AUD. A novel cell-based assay, a C-terminal CRFBP fragment [CRFBP(10 kD)] was developed and found to potentiates CRF-intracellular $Ca^{2+}$ release, demonstrating that CRFBP possesses excitatory roles in addition to the inhibitory role established by the N-terminal fragment of CRFBP [CRFBP(27 kD)]. This interaction was $CRF_2$-specific, as $CRF_1$ responses were not potentiated by CRFBP(10 kD). As there were currently no small molecule ligands available that selectively interact with either CRFBP or $CRF_2$, a cell-based assay was miniaturized, wherein CRFBP(10 kD) was fused as a chimera with $CRF_{2\alpha}$, that permitted a high-throughput screen (HTS) of approximately 350,000 small molecules. This resulted in the identification of negative allosteric modulators (NAMs) of the CRFBP(10 kD)-$CRF_2$ complex that blunt CRF-induced potentiation of N-Methyl-D-aspartic acid receptor (NMDAR)-mediated synaptic transmission in dopamine neurons in the ventral tegmental area (VTA).

In one embodiment, the present invention provides a compound of the formula:

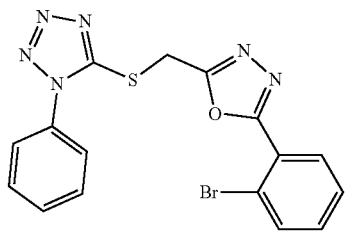 [SMILES: Brc1ccccc1-c1nnc(CSc2nnnn2-c2ccccc2)o1]

or a pharmaceutically-acceptable salt thereof. This compound is also referred to as MLS-0046818. In another embodiment, the present invention provides a pharmaceutical composition comprising a compound of the formula:

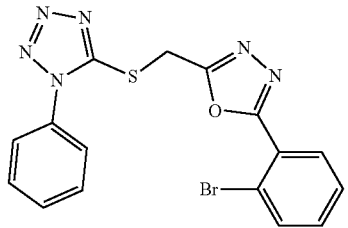 [SMILES: Brc1ccccc1-c1nnc(CSc2nnnn2-c2ccccc2)o1]

or a pharmaceutically-acceptable salt thereof, and one or more pharmaceutically-acceptable carriers, diluents, or excipients.

In alternate embodiment, the present invention provides a compound of the formula:

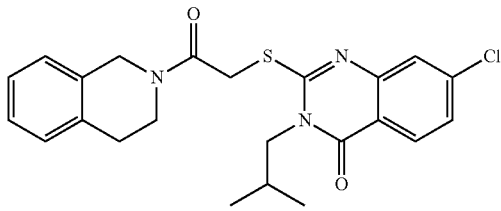 [SMILES: CC(C)Cn1c(SCC(=O)N2CCc3ccccc3C2)nc2cc(Cl)ccc2c1=O]

or a pharmaceutically-acceptable salt thereof. This compound is also referred to as MLS-0219419. In another embodiment, the present invention provides a pharmaceutical composition comprising a compound of the formula:

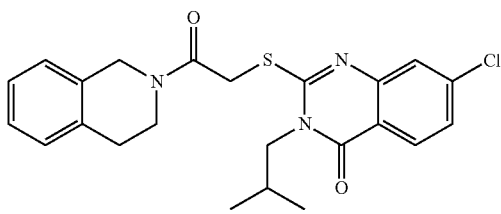 [SMILES: CC(C)Cn1c(SCC(=O)N2CCc3ccccc3C2)nc2cc(Cl)ccc2c1=O]

or a pharmaceutically-acceptable salt thereof, and one or more pharmaceutically-acceptable carriers, diluents, or excipients.

In yet another alternate embodiment, the present invention provides a method of treating alcohol use disorder comprising the step of administering to a subject, in need thereof, a composition comprising a therapeutically-effective amount of a negative allosteric modulator (NAM) of the CRFBP(10 kD)-CRF$_2$ complex. In some embodiments, the composition antagonizes and downregulates CRF-induced potentiation of N-Methyl-D-aspartic acid receptor (NM-DAR)-mediated synaptic transmission in dopamine neurons in the ventral tegmental area (VTA) of the subject. The NAM selectively antagonizes CRF at the CRFBP-CRF$_2$ complex but lack antagonistic activity toward CRF$_2$ alone and CRF$_1$.

In some embodiments, the NAM used in the methods of the present invention is a compound of the formula:

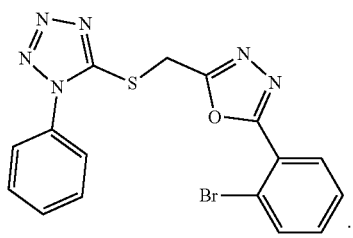 [SMILES: Brc1ccccc1-c1nnc(CSc2nnnn2-c2ccccc2)o1]

In alternative embodiments, the NAM used in the methods of the present invention is a compound of the formula:

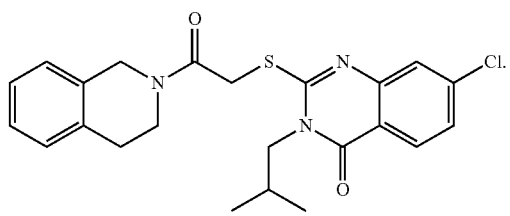 [SMILES: CC(C)Cn1c(SCC(=O)N2CCc3ccccc3C2)nc2cc(Cl)ccc2c1=O]

Other implementations are also described and recited herein.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings:

FIG. 1A: CRF produced a dose dependent stimulation of [$^{35}$S]GTPγS-binding FLAG-CRF-BP(10 kD)-HA-CRF$_{2\alpha}$. FIG. 1B: AS-30 inhibits CRF-stimulated (1 μM) [$^{35}$S]GTPγS FLAG-CRF-BP(10 kD)-HA-CRF$_{2\alpha}$ binding. The values are expressed as M±SEM percentage increase in basal [$^{35}$S]GTPγS binding.

FIG. 2A: Dose response curves for CRF-induced (1 pM-10 μM) intracellular calcium release in HEK293 cells expressing the FLAG-CRFBP(10 kD)-HA-CRF$_{2\alpha}$ (EC$_{50}$=451±1 nM). FIG. 2B: Inhibition of CRF-induced (1 μM) intracellular calcium release in HEK293 cells expressing CRFBP(10 kD)-CRF$_{2\alpha}$ by CRF$_2$ antagonist, AS-30 (2.2 nM-0.54 μM) (IC$_{50}$=27±1 nM). Results are expressed as the M±SEM relative fluorescence units (RFU), using 384-well assay format, calculated as agonist-induced maximum calcium peak/cell number×1000.

FIG. 3A-B depicts the quality control of cell-based assay expressing FLAG-CRFBP(10 kD)-HA-CRF$_2$. Assay quality control analysis from: FIG. 3A: 96-well format (Z'=0.62) and FIG. 3B: 384-well format (Z'=0.54) in HEK 293 cells stably expressing the CRFBP(10 kD)-CRF$_2$. CRF (1 μM)-induced intracellular calcium (maximum RFU, EC80 concentration) was consistently inhibited by AS-30 (1 μM) (minimum RFU), n=35. Results are expressed as the M±SEM relative fluorescence units (RFU), calculated as agonist-induced maximum calcium peak/cell number×1000.

FIG. 4A represented by the tetrazole-thiomethyl-oxadiazole-like MLS-0046818, and FIG. 4B represented by the quinazolinone-like MLS-0219419.

FIG. 5A: MLS-0046818 and FIG. 5B: MLS-0219419 dose-responses were performed in the presence of an EC$_{80}$ concentration of CRF in CRF$_1$ (Red), CRF$_2$ (Green), and CRFBP-CRF$_2$ (Blue) Ca$^{2+}$ assays. MLS-0046818 and MLS-0219419 only inhibit the CRFBP-CRF$_2$ response. Results are expressed as the M±SEM of the % of the EC$_{80}$ CRF Response.

Figure 6:
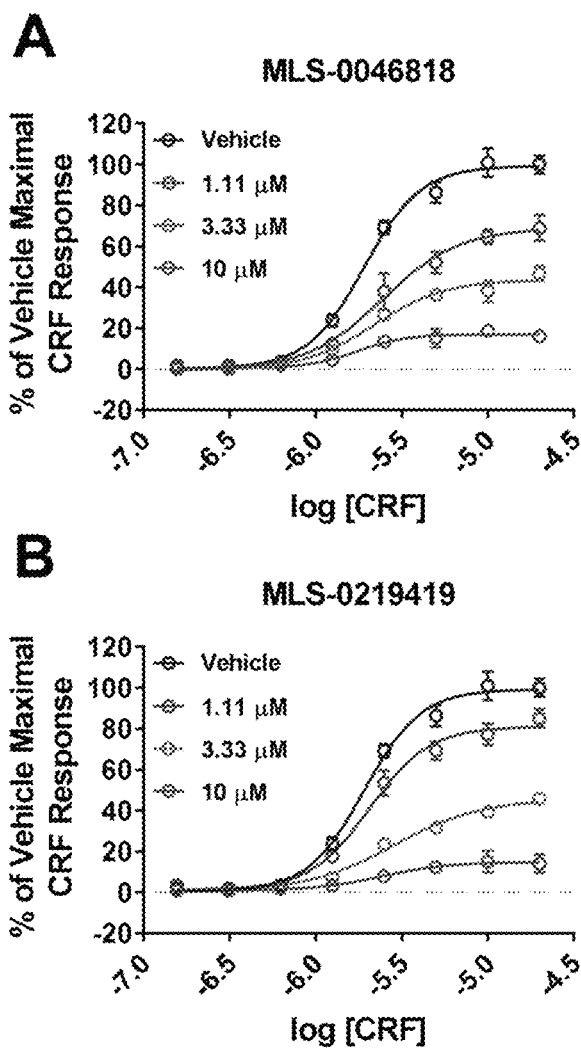
FIG. 6A-B shows that MLS-0046818 and MLS-0219419 noncompetitively antagonize CRF responses in CRFBP-CRF$_2$ Ca$^{2+}$ assays. CRF responses were performed (FIG.

6A) ±MLS-0046818 or (FIG. 6B) ±MLS-0219419 as indicated. CRF maximal responses are decreased with increasing concentrations of either MLS-0046818 or MLS-0219419. Results are expressed as the M±SEM of the % of the vehicle treated maximal CRF Response.

FIG. 7A-B shows the in vivo PK properties in mouse plasma. Mice were dosed 10 mg/kg i.p. with either MLS-0046818 (FIG. 7A) or MLS-0219419 (FIG. 7B) and drug levels were monitored over 24 hour in the mouse plasma. Each data point represents the blood plasma levels from three independent mice. Results are expressed as the M±SEM.

Figure 8:
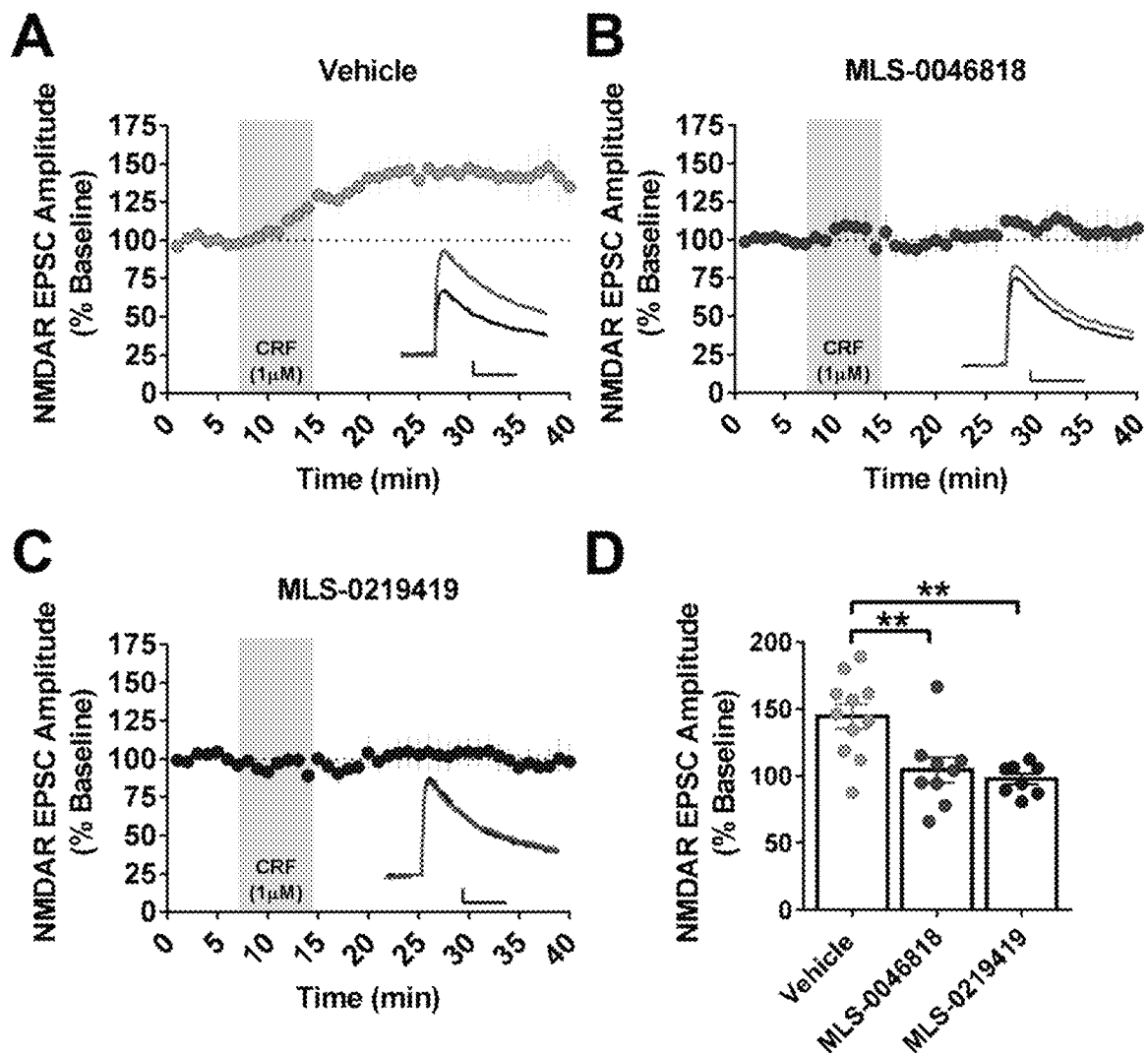

FIG. 8A-D shows the NMDAR potentiation by CRF and blockade by CRFBP-$CRF_2$ NAMs. FIG. 8A: CRF potentiated NMDA receptor EPSCs recorded from VTA-DA neurons (n=8, 11). 30 µM of (FIG. 8B) MLS-0046818 (n=4, 9) and (FIG. 8C) MLS-0219419 (n=4, 8) block CRF potentiation of NMDAR EPSCs. FIG. 8D: Summary of the M EPSC±SEM. The asterisk indicates significant differences between treatment and vehicle samples (**$p<0.01$), (n=mice, cells). Traces: Black, pre-CRF; Red, Post-CRF; Scale bar 25 pA/25 msec.

FIG. 9A-C depicts NMDAR potentiation by CRF and blockade by CRFBP-$CRF_2$ NAMs in male and female mice. FIG. 9A: There is no difference in male and female mice in CRF potentiated NMDA receptor EPSCs recorded from VTA-DA neurons (n=8, 11). 30 µM of (FIG. 9B) MLS-0046818 (n=4, 9) and (FIG. 9C) MLS-0219419 (n=4, 8) block CRF potentiation of NMDAR EPSCs with no difference between male and female mice. Results are reported as M EPSC±SEM. Differences are considered significant at *$p<0.05$, n.s. no significant, (n=mice, cells).

DETAILED DESCRIPTION OF THE INVENTION

It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The term "statistically significant" or "significantly" refers to statistical significance and generally means a two standard deviation (2SD) or greater difference.

As used herein, the term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

As used herein, the terms "effective amount" and "therapeutically-effective amount" include an amount sufficient to prevent or ameliorate a manifestation of disease or medical condition, such as alcohol use disorder (AUD). It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treating" or "treatment" or "to treat" or "alleviating" or "to alleviate" refer to both (1) therapeutic measures that cure, slow down, lessen symptoms of, and/or halt progression of a diagnosed disease or infection and (2) prophylactic or preventative measures that prevent or slow the development of a disease or infection.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a staticly significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

A subject can be one who has been previously diagnosed with or identified as suffering from or having a condition in need of treatment (e.g., AUD, alcohol intoxication, and alcohol abuse) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragées, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropyl methyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragées, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropyl methyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, micro-emulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically-acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art. See, e.g., Isselbacher et al. (1996).[11]

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In other embodiments, the active compound will be administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, I-ascorbic acid, I-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, I-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, I-pyroglutamic acid, salicylic acid, sebacic acid, stearic acid, succinic acid, sulfuric acid, I-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology and molecular biology can be found in The Merck Manual of Diagnosis and Therapy;[12] The Encyclopedia of Molecular Cell Biology and Molecular Medicine;[13] Molecular Biology and Biotechnology: a Comprehensive Desk Reference;[14] Immunology;[15] Janeway's Immunobiology;[16] Lewin's Genes XI;[17] Molecular Cloning: A Laboratory Manual.;[18] Basic Methods in Molecular Biology;[19] Laboratory Methods in Enzymology;[20] Current Protocols in Molecular Biology (CPMB);[21] Current Protocols in Protein Science (CPPS);[22] and Current Protocols in Immunology (CPI).[23]

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

Role of Stress and CRF in AUD

Many factors contribute to the development and maintenance of AUD and growing attention has been paid to the stress system as a pharmacological target for AUD.[24] Stress plays a critical role in the development and maintenance of AUD.[25] According to the 2015 National Survey on Drug Use and Health (NSDUH), AUD affects 15.1 million adults over age 18 in the United States[26] and alcohol is the fourth leading preventable cause of death.[27] Currently there are few Food and Drug Administration approved medications available (disulfiram, naltrexone and acamprosate) for treating AUD.[28] Disulfiram produces aversive effects after concurrent alcohol consumption by inhibiting ethanol metabolism[29] and is thought to enforce abstinence through this negative reinforcement. However, clinical trials with disulfiram have generated conflicting results and a recent meta-analysis does not support AUD efficacy.[30] The opioid receptor antagonist naltrexone is thought to modulate the mesolimbic dopamine (DA) reward pathway to help block the euphoria alcohol induces. While it decreases the amount and frequency of drinking,[31] it exerts only modest effects toward return to drinking and abstinence.[32,33,34] Acamprosate's mechanism of action (MOA) is not entirely defined[35] and provides only marginal improvements in alcohol-consumption outcomes.[36] Together, these interventions exhibit limited efficacy, have limiting contraindications[37] and none target the stress component. The impact of stress does not halt when individuals stop drinking. One of the most difficult aspects in treating AUD is relapse to drinking that can be triggered by stressful events after a period of abstinence.[38] Anxiolytic medications, antidepressants, and buspirone can reduce stress responses and are sometimes used off-label in the treatment of AUD; however, studies have reported inconsistent results.[39,40,41,42] The neurobiology of the stress response and its dysregulation by alcohol suggest additional potential pharmacological targets. These targets can lessen the response to acute stress in the central nervous system (CNS), thereby reducing the linkage between stress and alcohol consumption. For example, corticotropin releasing factor (CRF) receptor 1 ($CRF_1$) antagonists, which attenuate the neuroendocrine and behavioral responses to both acute and chronic stress, have shown efficacy to reduce alcohol seeking in preclinical models[43] but have had limited effects in clinical studies.[44,45] An effective treatment for AUD would ideally modulate the neurohormonal adaptations caused by an altered stress response, rather than antagonize the signal. Therefore, interventions that modulate CRF signaling rather than blocking it, as described in this proposal, may provide therapeutic benefit for AUD, where a critical unmet need remains.

The primary factor regulating the brain stress response is a 41-amino acid peptide known as corticotropin releasing factor (CRF), which exerts its effects on both the hypothalamic-pituitary-adrenal (HPA) axis and extrahypothalamic regions by binding to two receptors ($CRF_1$ and $CRF_2$) and a secreted 37-kD CRF binding protein (CRFBP).[46] The expression pattern of CRFBP in cortical and subcortical regions suggests a critical role in the modulation of stress responses.[47] CRFBP and $CRF_2$ are co-expressed in rat ventral tegmental area (VTA) glutamatergic synaptosomes that originate from hypothalamic areas.[48]

The ventral tegmental area (VTA) is a brain region that is critical for reward learning and is altered by nearly all known drugs of abuse. In addition, the VTA is critically involved in conditioned learning and the development of drug sensitization. Ethanol directly and indirectly modulates the output of VTA-DA neurons by enhancing firing rates via multiple mechanisms, subsequently leading to altered release of DA within its efferent brain regions. Suppressing the firing of VTA-DA neurons attenuates ethanol consumption and self-administration[49,50,51] and electrophysiological studies have shown that bath application of ethanol increases VTA-DA neuron firing rates.[52] Furthermore, rats will self-administer ethanol directly into the VTA. This effect can be blocked by quinpirole, a D2 receptor agonist which putatively inhibits VTA-DA activity.[53,54] These studies support the idea that ethanol in the VTA is rewarding and promotes activity of VTA-DA neurons. The activation of N-methyl-D-aspartate (NMDA) receptors (NMDARs), particularly on DA neurons in the VTA, leads to sustained $Ca^{2+}$-dependent long-term potentiation of synaptic plasticity. The activity of these VTA-DA neurons then further drives plasticity in efferent regions of the mesolimbic DA system. Behaviorally, NMDARs in the VTA are critical for reward learning.[55,56] Functionally, VTA NMDARs are required for DA neuron burst firing and phasic DA release in efferent brain regions.[57,58] The application of NMDA enhances overall burst firing of VTA-DA neurons in vitro in mice exposed to ethanol,[59] suggesting a role for NMDAR in ethanol-induced changes in VTA activity and providing an exquisite means of predicting functional and behavioral outcomes to alcohol use.

The intersection of stress and ethanol converges on CRF and the VTA mesolimbic DA system. Stressful stimuli release CRF from hypothalamic areas, activate DA neurons, and cause DA release in regions of the mesolimbic DA system. CRF exerts its effects through binding to two G protein-coupled receptors ($CRF_1$ and $CRF_2$, which has two isoforms $CRF_{2\alpha}$ and $CRF_{2\beta}$) and a 37-kD CRF binding protein (CRFBP).[60] Under homeostatic conditions, CRFBP binds all free CRF but during chronic stress, CRF release is augmented and CRFBP is unable to bind all of the released CRF.[61] Ethanol and other drugs of abuse often enhance VTA-DA neuronal firing. VTA-DA neurons display enhanced firing upon CRF application, mediated by alterations in intrinsic excitability and intracellular signaling,[62] suggesting that CRF may support enhanced VTA-DA firing during stress and substance seeking and consumption. Synaptically, NMDAR current amplitude is increased by application of CRF on acute brain slices.[63] Studies with CRFBP and $CRF_2$ blocking agents have shown that this requires the interaction of CRFBP with $CRF_2$, both of which are co-expressed in the rat VTA.[64] Together, these data suggest that CRFBP and $CRF_2$ are required to potentiate NMDAR responses and that CRF-mediated NMDAR amplitude potentiation provides a means of assessing CRF and CRFBP activity on VTA-DA neurons.

CRF release in the VTA supports alcohol seeking and administration[65,66] and in vivo ethanol exposure enhances NMDAR plasticity and responses to CRF.[67] In addition, blockade of CRFBP using a CRF analogue ($CRF_{6-33}$), thought to bind and block normal CRF-CRFBP interactions, or the use of a peptide $CRF_2$ antagonist is sufficient to block alcohol consumption following repeated self-administration.[68] Recent work has also shown that $CRF_2$ and CRFBP are expressed in the VTA, suggesting that this anatomical input plays a role in stress-induced relapse to drug-seeking behavior.[69] We recently demonstrated that the global loss of the CRHBP gene leads to increased ethanol consumption in the mouse drinking-in-the-dark (DID) model but only after repeated behavioral stress insults ($3^{rd}$ DID cycle; strong effects at $6^{th}$ DID cycle). This increased consumption under repeated stress is consistent with global rises in free CRF that are not sequestered by CRFBP. Alternatively, selective CRFBP downregulation in the extrahypothalamic area (e.g. center nucleus of the amygdala, CeA) decreases ethanol consumption in ethanol-dependent rats.[70] However, this reduction is lost after stress induction (yohimbine challenge), suggesting that CRFBP downregulation in the CeA was sufficient to blunt the ethanol drinking-behavioral phenotype, but insufficient during a stressful trigger. These data are consistent with studies reporting that microinjection of the CRFBP antagonist $CRF_{6-33}$ into the VTA, but not in the CeA, affect ethanol intake.[71] Together, these findings suggest that CRFBP in the VTA contributes to an escalation in ethanol drinking and that CRF may have more effects on DAergic rather than GABAergic transmission. We predict that peripheral CRF effects are attenuated by the circulating CRFBP (scavenger), while CRF release in the CNS, where CRFBP is membrane-bound and in close proximity with CRF receptors, will potentiate NMDAR currents during access to binge alcohol consumption, which can be attenuated by CRFBP-$CRF_2$ antagonists. These data support the hypothesis that blockade of the CRFBP interaction with $CRF_{2\alpha}$ may represent a novel class of drugs to treat AUD.

However, CRFBP has been far less investigated relative to $CRF_1$ and $CRF_2$. This is largely due to spontaneous proteolytic cleavage of the full length 37 kD CRFBP to an N-terminal 27-kD fragment [CRFBP(27 kD)] that binds CRF and C-terminal 10-kD fragment [CRFBP(10 kD)] that does not bind CRF.[72] We have recently investigated the role full length CRFBP and its proteolytic fragments individually play in CRF receptor signaling in vitro. In particular, we developed chimeric cell-based assays where $CRF_1$ and $CRF_{2\alpha}$ are expressed in the absence and presence of various tethered CRFBP constructs to evaluate the individual roles of the full length 37-kD CRFBP, CRFBP(27 kD), and CRFBP(10 kD) on $CRF_1$ and $CRF_{2\alpha}$ signaling. These studies revealed that only CRFBP(10 kD) tethered to $CRF_{2\alpha}$ potentiates CRF-mediated $Ca^{2+}$ signaling, while CRFBP(27 kD) has an inhibitory role. Comparing maximal efficacy ($E_{max}$) values, CRFBP(10 kD)-$CRF_{2\alpha}$ potentiates CRF-induced signaling compared to $CRF_{2\alpha}$ alone, which is not due to changes in receptor expression. Alternatively, comparing potency, CRFBP(10 kD)-$CRF_{2\alpha}$ requires a higher level of CRF ($EC_{50}$=385 nM) to see potentiation (as would occur under stress activation) relative to $CRF_{2\alpha}$ alone ($EC_{50}$=99 nM). These results support the hypothesis that $CRF_{2\alpha}$ in the presence of CRFBP(10 kD) is only potentiated during stress induction where there is increased free CRF. Our data suggest a dual role for CRFBP where CRFBP(27 kD) acts to inhibit CRF effects and where CRFBP(10 kD) has a potential excitatory function.[73] While there is no direct evidence that the interaction of CRFBP(10 kD) with $CRF_{2\alpha}$ is physiologically relevant, molecular dynamics simulations by our group[74] and others[75] show protein-protein docking interactions of CRF and the C-terminal domain of CRFBP [CRFBP (10 kD)]. $CRF_{2\alpha}$ is exclusively expressed in the CNS, while $CRF_{2\beta}$ is peripherally expressed and regulates homeostatic behavior. CRFBP also physically interacts with $CRF_{2\alpha}$ but not $CRF_{2\beta}$, increasing cell surface $CRF_{2\alpha}$.[76] To further support a role for CRFBP(10 kD) signaling, we have discovered that a series of single nucleotide polymorphisms (SNPs) located in the human gene region that are associated with increased risk of AUD, neuroticism, and anxiety.[77] During chronic stress, excess CRF activates $CRF_{2\alpha}$ and we hypothesize that CRFBP(10 kD) cleaves off CRFBP and allosterically potentiates $CRF_{2\alpha}$ signaling. Our screening assay specifically targets this possible conformational change of $CRF_{2\alpha}$ during stress conditions. Thus, the CRFBP (10 kD)-$CRF_{2\alpha}$ complex (referred to hereafter as CRFBP-$CRF_2$) may provide a novel therapeutic target for the treatment of AUD.

CRFBP interacts with $CRF_2$ and increases cell surface $CRF_2$ expression,[78] and we have shown that CRF modulates synaptic input by potentiating N-methyl-D-aspartate (NMDA)-mediated excitatory postsynaptic currents through CRFBP/$CRF_2$ interactions in the VTA.[79] CRFBP has been shown to play a key role via $CRF_2$ in both the modulation of ethanol consumption[80] and cocaine seeking.[81] We have also recently demonstrated that loss of the CRFBP gene CRHBP leads to increased ethanol consumption in mice, and that a selective downregulation of CRHBP in the center nucleus of the amygdala (CeA) decreases ethanol consumption in ethanol-dependent rats,[82] providing the initial evidence that CRFBP may possess both inhibitory and excitatory roles. Together, these data support the hypothesis that CRFBP possesses additional functions beyond sequestration of CRF and that its interaction with $CRF_2$ may represent a novel pharmacological target for the treatment of AUD.

Main Objectives of the Present Invention

As described above, many factors contribute to the development and maintenance of AUD and growing attention has been paid to the stress system as a pharmacological target for AUD.[83] The primary factor regulating the brain stress response is a 41-amino acid peptide known as corticotropin releasing factor (CRF), which exerts its effects on both the hypothalamic-pituitary-adrenal (HPA) axis and extrahypothalamic regions by binding to two receptors ($CRF_1$ and $CRF_2$) and a secreted 37-kD CRF binding protein (CRFBP).[84] The expression pattern of CRFBP in cortical and subcortical regions suggests a critical role in the modulation of stress responses.[85] CRFBP and $CRF_2$ are co-expressed in rat ventral tegmental area (VTA) glutamatergic synaptosomes that originate from hypothalamic areas.[86] CRFBP interacts with $CRF_2$ and increases cell surface $CRF_2$ expression,[87] and we have shown that CRF modulates synaptic input by potentiating N-methyl-D-aspartate (NMDA)-mediated excitatory postsynaptic currents through CRFBP/$CRF_2$ interactions in the VTA.[88] CRFBP has been shown to play a key role via $CRF_2$ in both the modulation of ethanol consumption[89] and cocaine seeking.[90] We have also recently demonstrated that loss of the CRFBP gene CRHBP leads to increased ethanol consumption in mice, and that a selective downregulation of CRHBP in the center nucleus of the amygdala (CeA) decreases ethanol consumption in ethanol-dependent rats,[91] providing the initial evidence that CRFBP may possess both inhibitory and excitatory roles. Together, these data support the hypothesis that CRFBP possesses additional functions beyond sequestration of CRF and that its interaction with $CRF_2$ may represent a novel pharmacological target for the treatment of AUD.

The functional role of CRFBP is less well-understood than that of the two primary CRF receptors because 37-kD CRFBP is spontaneously cleaved into an N-terminal 27-kD fragment [CRFBP(27 kD)] that binds CRF and a C-terminal 10-kD fragment [CRFBP(10 kD)] that does not bind to CRF.[92] To dissect the respective functional roles of the full-length CRFBP and its two fragments, we developed novel chimeric cell-based assays by stably expressing each CRFBP construct tethered to $CRF_2$ or $CRF_1$. We found that only the CRFBP(10 kD) tethered to $CRF_2$ is able to potentiate CRF-mediated $Ca^{2+}$ mobilization.[93] Our findings suggest a dual role for CRFBP: 1.) CRFBP(27 kD) acts to block CRF effects, and 2.) CRFBP(10 kD) has a potential excitatory function.[94] Based on these findings, we utilized a novel CRFBP-$CRF_2$ assay in a high-throughput screen of ~350,000 compounds to identify CRFBP-$CRF_2$ modulators and identified a lead and backup series of compounds with in vitro activity as negative allosteric modulators (NAMs) of the CRFBP-$CRF_2$ complex only in the presence of CRFBP (10 kD).[95] Chemical probes specific for the CRFBP-$CRF_2$ complex are needed to elucidate the biological function of CRFBP(10 kD) and its interaction with $CRF_2$. These probes would allow us to establish the role of CRFBP in alcohol consumption and facilitate the development of effective treatments targeting CRFBP for AUD. Thus, the overall objective was to develop orally active CRFBP-$CRF_2$ NAMs suitable for advanced in vivo proof-of-concept studies for the treatment of AUD.

As described herein, we have performed a high-throughput screen (HTS) (see Example 3) to discover CRFBP-$CRF_2$ modulators and have identified a lead and backup series of compounds with in vitro activity as negative allosteric modulators (NAMs) of the CRFBP-$CRF_2$ complex. Importantly, these compounds do not affect $CRF_1$ or $CRF_2$ in the absence of the CRFBP(10 kD). As described herein, the molecular target of our NAMs is CRFBP(10 kD) tethered to the CNS specific CRF receptor isoform $CRF_{2\alpha}$ and not $CRF_{2\beta}$ which is peripherally expressed and regulates homeostatic behavior. In fact, because CRFBP physically interacts with $CRF_{2\alpha}$ but not $CRF_{2\beta}$[96] and the compounds of the present invention do not affect $CRF_1$ or $CRF_2$ alone, this pharmacology has the potential advantage of not affecting feeding behavior and energy homeostasis. The development of optimized CRFBP-$CRF_2$ probes would provide tools to elucidate the molecular function of CRFBP(10 kD) and its interaction with $CRF_2$, will allow us to investigate the role of CRFBP-$CRF_2$ in alcohol consumption, and facilitate the development of effective treatments targeting CRFBP-$CRF_2$ for AUD. Thus, the overall objective was to develop orally active CRFBP-$CRF_2$ NAMs suitable for the treatment of AUD. The ideal profile for CRFBP-$CRF_2$ NAMs is provided in Table 1.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

TABLE 1

Ideal Profile of CRFBP-CRF2 NAMs

| Parameter | | Criteria |
|---|---|---|
| CRFBP-$CRF_2$ $IC_{50}/EC_{50}$ ($Ca^{2+}$ assay) | | <500 nM |
| Fold Selectivity vs. $CRF_1$ and $CRF_2$ | | >50 fold |
| Plasma stability | | >75% at 1 hr |
| Microsomal stability (HLM, RLM, MLM) | | >75% at 1 hr |
| $t_{1/2}$ (p.o., mouse) | | >2 h |
| Oral bioavailability (mouse) | | >30% |
| Unbound Clearance (mouse) | | <30 mL/min/kg |
| Exposure (AUC, mouse, p.o.) | | >1000 μM*min |
| Brain levels at $T_{max}$ (mouse) | | 10 × $IC_{50}$ |
| Plasma Protein Binding | | <95% |
| Brain Homogenate Binding | | <98% |
| Solubility | | >10 mg/mL |
| CYP450 inhibition | 1A2 | $IC_{50}$ > 10 μM |
| | 2C9 | |
| | 2D6 | |
| | 3A4 | |
| Off-Target Selectivity (PDSP, Eurofins) | | <50 fold |
| Drug transporter substrate $P_{app}$ (A/B) (MDR-1) | | >5 × $10^{-6}$ cm/s |
| Ex vivo efficacy: Ethanol Naive VTA-DA NMDAR EPSCs | | Active |
| Ex vivo efficacy: DID Model VTA-DA NMDAR EPSCs | | Active |

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention, and are not intended to limit the invention.

Example 1 Materials and Methods

Materials

Materials and methods for the CRFBP-CRF receptor chimeras are extensively described in Haass-Koffler, et al. (2016).[97] CRF, and the $CRF_2$ specific inhibitor, antisauvagine 30 (AS-30, #A4727) were acquired form Sigma-Aldrich (St. Louis, Mo., US), FLIPR Calcium Assay Kits were purchased from Molecular Devices (Sunnyvale, Calif., US), and 96-well plates (black wall, clear bottom, BIO-COAT, #08774256) were purchased from Thermo Fisher Scientific (Waltham, Mass., US). [$^{35}$S]-Guanosine 5'-(γ-thio) triphosphate ([$^{35}$S]-GTPγS) (250 µCi; 9.25 MBq) was supplied from Perkin-Elmer® (Boston, USA). Guanosine 5'-[γ-thio]triphosphate tetralithium salt (GTPγS), guanosine 5'-diphosphate sodium salt (GDP), 2-hydroxy-ethylpiperazine-N-2-ethane sulphonic acid (HEPES), DL-dithiothreitol, tricine, magnesium chloride ($MgCl_2$) ethylenediaminetetraacetic acid (EDTA) and saponin were purchased from Sigma-Aldrich® (St. Louis, USA). Complete mini protease inhibitor cocktail tablets were purchased from Roche (Indianapolis, USA). Wheatgerm agglutinin SPA Beads were purchased from Amersham (Little Chalfont, England) Biosciences. The cell culture, generation of stably transfected fusion plasmids, transfection and expression of human cells with the CRFBP-CRF receptor chimeras, cell selection and flow cytometry, western blots, immunofluorescence, image analysis, quantification of receptor surface expression by ELISA and fluorescence-based calcium assay are extensively described in Haass-Koffler, et al. (2016).[98]

[$^{35}$S]-GTPγS Binding Assay

HEK293 cells stably expressing the FLAG-CRFBP(10 kD)-HA-$CRF_2$ chimera and maintained at 37° C., 7% $CO_2$ were suspended in a homogenization buffer (50 mM Tris-HCl, 1 mM EDTA, 3 mM $MgCl_2$ pH 7.4; 1 g brain tissue/20 mL buffer). Cell suspensions were centrifuged (14000 rpm, 15 minutes, 4° C.) and pellets were resuspended in the homogenization buffer, sonicated on ice, recentrifuged and resuspended in HME assay buffer (pH 7.5; 100 mM HEPES.NaOH, 10 mM NaCl, 5 mM $MgCl_2$, 10 µg/mL saponin and one mammalian protease inhibitor tablet/25 mL). Binding assays were performed in 96-well plates in quadruplicate on ice with each reaction containing [$^{35}$S] GTPγS (50 pM), cell membrane (10 µg protein), GDP (30 µM), and SPA beads (0.5 mg) with HME assay buffer and the CRF ligands. Non-specific binding was determined in the presence of unlabeled GTPγS (10 µM). Single drug dose-response curves of [$^{35}$S]GTPγS stimulated binding were performed with CRF (10 nM-10 µM) and inhibition of CRF-R2-mediated [$^{35}$S]GTPγS stimulation was performed with CRF (1 µM; $EC_{80}$) and AS-30 (10 nM-10 µM). Membranes and GDP were incubated together for 20 minutes and then AS-30 was added 30 minutes prior to addition of CRF, before the [$^{35}$S]-GTPγS and SPA beads were added. Assay plates were shaken for 45 minutes at 25° C., and centrifuged (1500 rpm, 5 minutes, 25° C.) before [$^{35}$S]GTPγS stimulated binding was assessed using the NXT TOPCOUNTER™. [$^{35}$S]GTPγS-stimulated binding is expressed as a percentage increase in basal [$^{35}$S]GTPγS binding.

Miniaturization

The calcium assay volumes from the 96-well plate format described above, in 384 well plates were reduced as follows: cells 15 µL, FLIPR dye 15 µL, AS-30 7.5 µL, CRF 7.5 µL, for a total of 45 µL.

Calcium Assay in 384 Well Plates

HEK293 cells stably expressing the chimeras (CRFBP-$CRF_{2\alpha}$ or CRFBP-$CRF_1$) or individual receptors ($CRF_{2\alpha}$ or $CRF_1$) were thawed out from liquid nitrogen quickly at 37° C. They were spun down in falcon tube at 800 rpm for 12 minutes. Three vials worth of 6 million cell/mL were resuspended in 15 mL media containing 10% FBS/DMEM and placed into T75 flask and incubated at 37° C. for 3 days. When cells reached ~70-80% confluent in flask, the media was removed, and the cells were washed with 5 mL PBS without calcium or magnesium. After PBS was removed, another 5 mL PBS was added (no magnesium or calcium) and the flask was allowed to sit for 5 minutes. Cells were washed off the glass surface with pipette and transferred to 15 mL falcon tube. The cells were spun down at 800 rpm for 12 minutes and resuspended in 5 mL 10% FBS/DMEM. The cell density was calculated using nucleocounter. The final concentration of 600,000 cells per mL was achieved by adding extra volume of 10% FBS/DMEM. 50 µl cell suspension per well into 384 well plates (30000 cells per well) was platted out and the cells were left to settle in plate at 37° C. for 2 days. On day of testing, the media was removed from each well and 50 µl PBS (no calcium or magnesium) was added per well to wash cells. The PBS was removed and 15 µl of 1% FBS/DMEM per well was added. Fresh assay buffer was made as follows for 100 mL buffer: 10× Hanks Balanced Salt Solution (HBBS), 10 mL HEPES 1 M, 2 mL distilled water, 87 mL 100× Probenecid solution (250 mM), 71 mg dissolved in 1 mL 1 N NaOH, Bovine Serum Albumin (for 0.1% final) 100 mg, set pH to 7.4. 1 vial FLIPR Calcium dye was diluted in 10 mL assay buffer and resuspended per assay plate. 15 µL of dye was added to each well in 384-well plates and incubated for 1 hour at 37° C. For stimulation assays, compound plate was made at 50 µM (5× for 7.5 µL injection onto 30 µL, i.e., 37.5 µl total volume per well after injection) to give final concentration of 10 µM per well. So for 2 µL of a 1 mM solution in the compound plate, it was added 38 µL of buffer (i.e., 1 in 20 dilution). After addition onto cell plate, the final concentration of DMSO was 1%. CRF (MW=4757.45; source from Sigma) is in 0.5 mg vials. For a 1 mM stock solution, 105 µL distilled water was added. The assay was run on FLEXSTATION at 21° C. (50 minutes for 384-well plate at 2 minutes for each column of 16 wells at a time). For inhibition assay, a new compound plate with agonist (CRF) was prepared at 6×. For the pre-determined $IC_{80}$ concentration to inhibit of 1 µM of CRF, a 6 µM solution with a 40 µL volume per well (16 mL of 6 µM solution of CRF per plate) was prepared for a 7.5 µL injection onto 37.5 µL (45 µL total volume per well after injection) to give a final concentration of 1 µM CRF.

Primary High-Throughput and Confirmation Screening

CRFBP-$CRF_2$ HEK293 cells (1,000 cells/6 µL per well) were plated in 1536-well black walled clear-bottom Poly-D-Lysine coated plates (Corning) in Assay Media (Dulbecco's Modified Eagle Medium (DMEM) (1×), phenol red free, 1% Defined Fetal Bovine Serum (FBS) (Hyclone), 1× Penicillin/Streptomycin (P/S), and 1× L-Glutamine) using a Multidrop Combi (Thermo). Cell plates were spun at 500 rpm for 1 minute in a centrifuge, covered with Kalypsys lids, and incubated overnight at 37° C. in the presence of 5% $CO_2$. The following day, 2 µL per well of FLIPR Calcium 4 Dye (Molecular Devices), prepared in Assay Buffer (1× Hanks' balanced salt solution, 20 mM HEPES, 0.1% Bovine Serum Albumin [Sigma], and 2.5 mM probenecid [Sigma], pH 7.4) was added to each well of the assay plate at 0.5× according to the Manufacturer's Instructions using the Multidrop Combi (Thermo) dispenser and the cells were incubated in dye for 1 hour 37° C. in the presence of 5% $CO_2$. Reagents are from Invitrogen unless otherwise stated.

Calcium flux was measured using a Functional Drug Screening System 7000 (FDSS7000; Hamamatsu, Tokyo, Japan). Baseline readings were taken (9 images at 1 Hz; excitation, 470±20 nm; emission, 540±30 nm), and then test compounds (approximately 53 nL) were added at the 10 second time-point using the FDSS's integrated 1536 well pin-tool from source library plates (Corning) containing 2 mM test compound stocks in 100% DMSO. Following this, at the 243 second time-point, 1 µL per well of either a maximal CRF response (4.5 µM Final, prepared as a 9× stock in Assay Buffer), $EC_{80}$ CRF response (1 µM Final, prepared as a 9× stock in Assay Buffer), or vehicle response (Assay Buffer) were added to appropriate wells using the FDSS's integrated 1536 well tips. Agonist "Hits" were selected by comparing the amplitude of the responses at the time of test compound addition to the CRF maximal response on each plate. Compounds were tested at 13.25 µM for agonist responses and those with responses ≥50% of the CRF maximal response were selected as hits for further study. Antagonist "Hits" were selected by comparing the amplitude of the responses at the time of $EC_{80}$ CRF addition±test compounds. Compounds were tested at 11.78 µM for antagonist responses and those compounds that inhibited >50% of the CRF $EC_{80}$ response were selected as hits for further study.

For confirmation screening, the CRFBP-$CRF_2$ $Ca^{2+}$ assay was performed in the identical as the primary screen with the following exceptions. For each test compound, eight assay plates were prepared, each of which received a different concentration of test compound by pin-tool in the FDSS7000 $Ca^{2+}$ assay. For the agonist confirmation screening, compounds were tested at 53.0 µM, 26.5 µM, 13.3 µM, 6.63 µM, 3.31 µM, 1.66 µM, 0.828 µM, and 0.414 µM. For the antagonist confirmation screening, compounds were tested at 47.1 µM, 23.6 µM, 11.8 µM, 5.89 µM, 2.94 µM, 1.47 µM, 0.736 µM, and 0.368 µM. Agonist $EC_{50}$ values were determined in the absence of CRF and antagonist $IC_{50}$ values were determined in the presence of an $EC_{80}$ concentration of CRF from each set of eight plates.

Z' Score Calculation for Quality Control

The Z-factor is established from four parameters: the means (µ) and standard deviations (σ) of both the positive (p) and negative (n) controls ($\mu_p$, $\sigma_p$, and $\mu_n$, $\sigma_n$). Z-factor is computed as:

$$Z\text{-factor}=1-3(\sigma_p+\sigma_n)/|\mu_p-\mu_n|$$

A Z' factor between 0.5 and 1.0 has been shown to represent a robust and reliable assay.[99]

In Vivo Pharmacokinetic Studies

Male C57BL/6J mice (n=9 for each compound), weighing approximately 20 to 30 g, were purchased from Jackson Labs (Bar Harbor, Me.) and were acclimated to their surroundings for approximately 1 week before dosing and provided food and water ad libitum. To measure systemic plasma and brain exposure, MLS-0046818 was administered intraperitoneally (i.p.) in 5% DMSO, 10% Tween80 in water, pH 7.0 and MLS-0219419 was administered i.p. in 5% DMSO, 10% Tween80, 20% (2-hydroxypropyl)-beta-cyclodextrin (HPBCD) in water, pH 7.0. Both compounds were administered as 1 mg/mL stock solutions in a dose volume of 10 mL/kg for a 10 mg/kg dose. Blood samples were collected via retro-orbital bleeds at 0.25, 0.5, 1, 2, 4, 6, and 24 hour. Whole brains were collected at 4, 6, and 26 hour. Whole blood was collected into EDTA-fortified tubes, centrifuged for 10 minutes at 14000 rpm, and the resulting plasma was collected and stored at −80° C. until LC/MS/MS analysis. Brain samples were rinsed in phosphate-buffered saline, snap-frozen, and stored at −80° C. Prior to LC/MS/MS analysis, brain samples were thawed to room temperature and subjected to mechanical homogenization using a Fisher PowerGen 125 (Fisher Scientific) on ice. Pharmacokinetic parameters were obtained from non-compartmental analysis (PkSolver[100]) of concentration-time profiles after test article administration.

Electrophysiology

Male and female mice (n=44; 6-10 weeks) were anesthetized with Euthasol (Butler-Schein). Brains were rapidly removed and placed in ice-cold NMDG-based artificial Cerebrospinal Fluid (aCSF) cutting solution containing (in mM): 92 NMDG, 20 HEPES, 25 glucose, 30 $NaHCO_3$, 2.5 KCl, 1.2 $NaPO_4$ saturated with 95% O2/5% CO2 with an osmolarity of 305-308 mOsm (Advanced Cell Diagnostics). The brain was cut in ice-cold NMDG solution to obtain horizontal VTA slices, 230 µm thick, using a Leica vibratome (Leica VT1200) and slices were incubated in warm NMDG solution (34° C.) for <5 minutes before being placed in a modified aCSF holding solution (in mM): 92 NaCl, 20 HEPES, 25 glucose, 30 $NaHCO_3$, 2.5 KCl, 1.2 $NaPO_4$ (305-308 mOsm). Slices were incubated at room temperature for at least 1 hour before recording.

Whole-cell patch clamp of the lateral VTA was performed under the guidance of IR-DIC optics on an Olympus BX5iWI microscope. Cells were patched with 1.8-3 MΩ resistance glass microelectrodes containing the following internal solution (in mM): 117 cesium methanesulfonate, 20 HEPES, 0.4 EGTA, 2.8 NaCl, 5 TEA-Cl, 4 Mg-ATP, 0.4 Na-GTP, and 5 QX-314 (280-285 mOsm). Dopamine cells were identified by the following criteria: 1) large multipolar soma, 30-40 µm in diameter, 2) tonic firing of <4 Hz when cell attached, 3) large lh current with negative voltage step (identified immediately following break in). Slices were perfused at a rate of 1.5-2 mL per minute with aCSF containing (in mM): 126 NaCl, 2.5 KCl, 1.4 $NaH_2PO_4$, 1.2 $MgCl_2$, 2.4 $CaCl_2$, 25 $NaHCO_3$, and 11 glucose (305-308 mOsm) in the presence of picrotoxin (100 uM) to block $GABA_A$ receptors and DNQX (10 uM) to block AMPA receptors. NMDA receptor currents were evoked with a bipolar stimulating electrode (FHC) held at +40 mV, filtered at 1 kHz with a Bessel filter, and were allowed to stabilize for 5 minutes before recording began. Drugs were washed on for 10 minutes prior to CRF application and for 2 minutes following application. Series resistance was monitored online. If series changed more than 20%, the recording was discarded.

Data Analysis

For the calcium assay, the data output contains a pre-assay scan of the plate and the maximum fluorescence observed over the 2-minute read per well. The data are presented as the Relative Fluorescence Units (RFU) calculated as: fluorescence value/pre-assay value×1000000. The Z-value was determined from each plate using the mean±SD RFU values of CRF (1 µM) alone and CRF (1 µM) with AS-30 (10 µM) (i.e., in presence of the CRF receptor inhibitor), as described before. The stimulation assay was analyzed as a percentage of the mean RFU value of CRF (1 µM) alone (i.e., CRF=100% stimulation). The inhibition assay was analyzed as the difference between the mean RFU value for CRF (1 µM) alone and the RFU of CRF (1 µM) in the presence of the inhibitor compound (AS-30 provides 100% inhibition). For inhibitor hits, >70% inhibition of CRF (from second assay run) was sought, but without any stimulation on its own (from first assay run). Comparisons between groups were performed using unpaired students t-test. Data are presented as mean (M)±standard error (SEM). The [$^{35}$S]-GTPγS bound (fmol/mg) was calculated based on the [$^{35}$S]-GTPγS radioactivity, $B_{max}$ and CPMs of CRF treatment relative to untreated. [$^{35}$S]-GTPγS stimulated binding by AS-30 either alone or in combination with CRF agonists, was assessed using each of $CRF_2$ and $CRF_1$-containing membranes. Differences are considered significant at *p<0.05.

For electrophysiology measures, excitatory post-synaptic currents (EPSCs) were normalized to 7 minute of averaged baseline responses, prior to drug application. All points are averaged per minute display. Results are reported as M±SEM a in bar graphs comparing drug to vehicle and analyzed by a one-way ANOVA and post-hoc comparisons to vehicle were performed using a Bonferroni multiple comparisons correction measures (**p<0.01). For single comparisons across sex, two-tailed t-tests were used. All statistical tests were two-sided. SPSS (v.22) (Armonk, N.Y., USA) was used to conduct the analysis and GraphPad Prism (v.7) was used to generate figures (La Jolla, Calif., USA).

Figure 1:
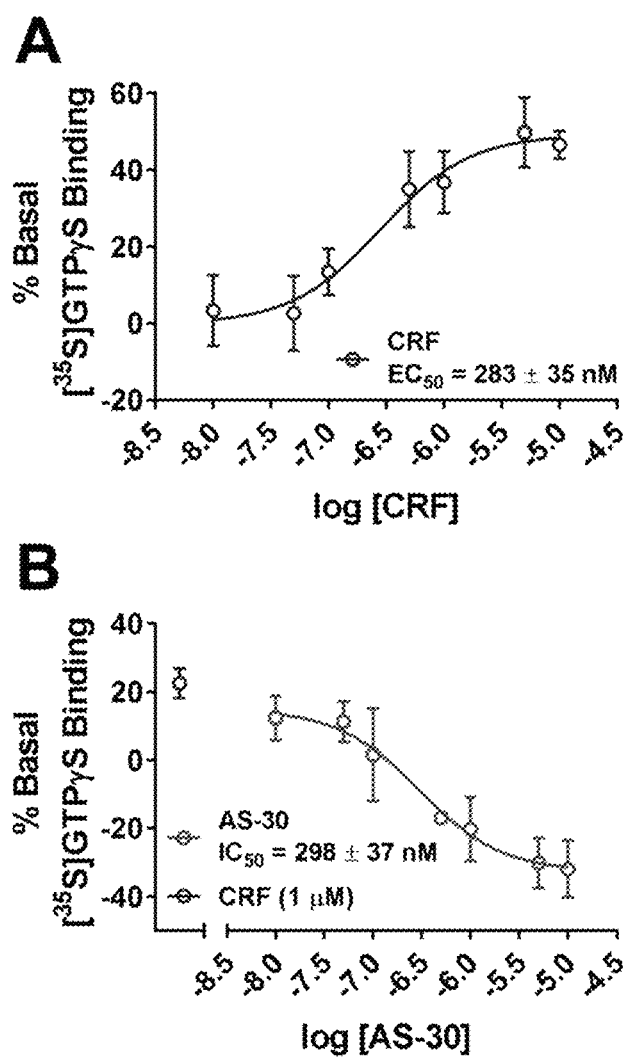
FIG. 1A-B shows the optimization of a cell-based assay expressing FLAG-CRFBP(10 kD)-HA-CRF$_{2\alpha}$ using the [$^{35}$S]GTPγS binding assay.

Example 2 Optimization and Miniaturization of the CRFBP-CRF2 Calcium Assay in 384-Well Plate Format We recently published on the construction of a CRFBP-$CRF_2$ chimeric complex and showed that this complex potentiates CRF-induced release of intracellular $Ca^{2+}$ in 96-well fluorescence-based calcium assays.[101] In order to further validate signaling from the CRFBP-$CRF_2$ chimeric complex, CRF-mediated coupling of the chimera was measured in [$^{35}$S]GTPγS binding assays to provide a convenient measure of $CRF_2$ activity at the closest proximity to the receptor in the signaling cascade (FIG. 1). CRF produced a dose-dependent stimulation of [$^{35}$S]GTPγS-binding in cell membranes expressing the FLAG-CRFBP(10 kD)-HA-$CRF_{2\alpha}$ chimera ($EC_{50}$=283±35 nM) (FIG. 1A). Furthermore, when CRF-stimulated (1 µM) [$^{35}$S]GTPγS-binding was performed in the presence of AS-30 (10 nM-10 µM), the binding was inhibited ($IC_{50}$=298±37 nM) (FIG. 1B).

Figure 2:
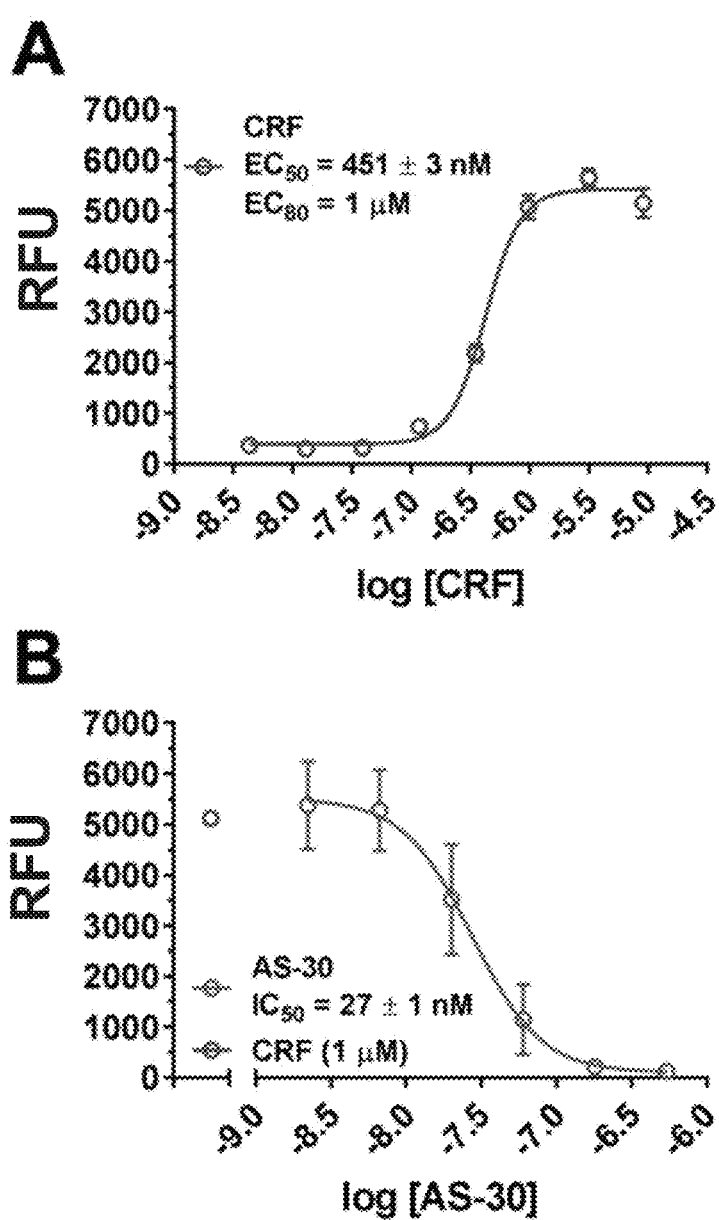
FIG. 2A-B shows the miniaturization of the calcium assay in 384-well format.

To improve the throughput and to increase HTS readiness for implementation, the assay was scaled from the original 96-well to a 384-well format (FIG. 2). Starting from the previously-described optimized 96-well conditions,[102] we used a total assay volume of 25-40 µL with 30,000 cells per well. The dye loading and pre-incubation times of antagonists and instrument settings for the FlexStation3 were identical to those for 96-well format. CRF-induced dose-dependent release of intracellular calcium ($EC_{50}$=451±3 nM, $EC_{80}$=1 µM), as shown in FIG. 2A, and AS-30 dose-dependently inhibited CRF- (3 µM) induced intracellular $Ca^{2+}$ release ($IC_{50}$=27±1 nM), as shown in FIG. 2B.

Figure 3:
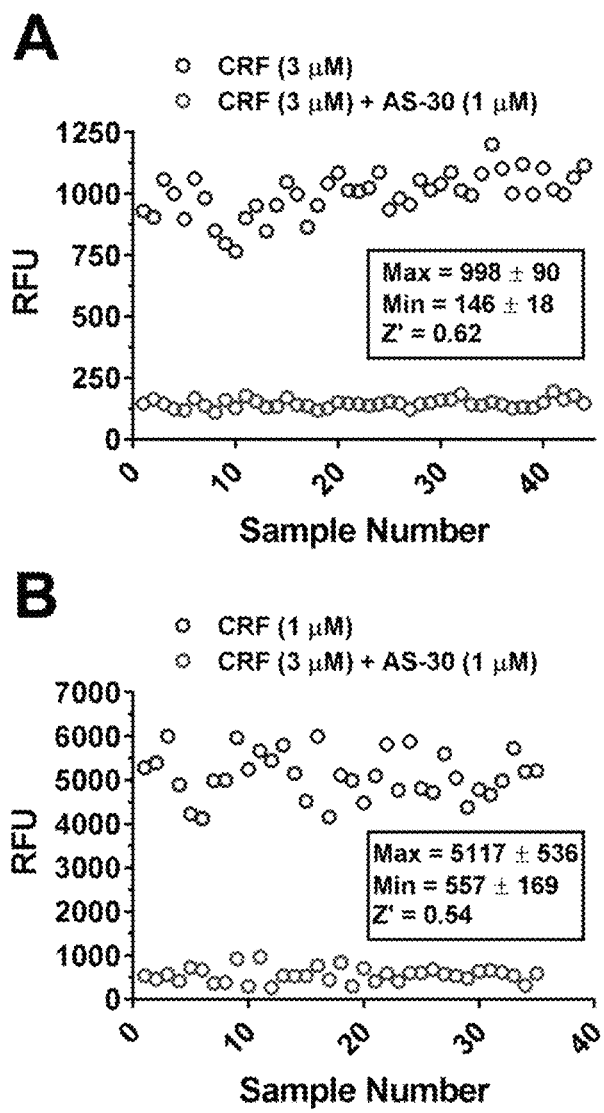

To assess the quality of the screening data in the 96-well and 384-well formats, the Z' factors were calculated for each plate and for the entire experiment, as previously reported[103] (FIG. 3). Under the described 96-well experimental conditions (50,000 cell per well, 3 M CRF±1 µM AS-30), the Z' factor for the quality control assay in 96-well format was 0.62 (FIG. 3A). Alternatively, a value of 0.54 (FIG. 3B) was achieved using the experimental conditions described above (30,000 cells and 1 µM CRF±1 µM AS-30 per well) in 384-well format, showing that the signal did not significantly degrade during the miniaturization process.

A pilot screen of the Library of Pharmacologically Active Compounds (LOPAC, SIGMA) was then configured to test the performance of the HTS in 384-well format. LOPAC consists of 1280 small molecules of known structure and generally assigned function, but of unknown activity with respect to CRFBP-$CRF_2$. Primary screening was conducted as described in Example 1. Compounds that inhibited the assay by >50% were considered "hits" (data not shown). For >70% inhibition, the hit rate for 1,280 compounds was 28%. The maximum signal for the assay was 5,921±158 RFU while the minimum signal for the assay was −250±28 RFU. As a control experiment, the inhibition of CRF (1 µM) was tested again prior to the library screening. Since one of our goals was to develop probes to investigate the interaction of CRFBP(10 kD) with $CRF_2$ in order to understand the physiological role of CRFBP in the central nervous system (CNS), we tested compounds in a primary screen for stimulation prior to the CRF inhibition screen assay. Compounds that produced >10% stimulation (compared to the RFU of CRF 1 µM in the same assay plate) in the primary screen were excluded. This was necessary for "weeding-out" false positive compounds that produced interference with intracellular calcium homeostasis. The average Z' factor across all the plates was determined to be 0.52 for the antagonist assay and 0.66 for the agonist assay.

Transfer of the Flexstation 384-Well Assay to the FDSS 7000 System

The assay was transferred to a Hamamatsu FDSS 7000 multimodal (fluorescence and luminescence) kinetic imaging system capable of measuring intracellular calcium flux in both 384 and 1534-well formats at the drug discovery facility at the Sanford Burnham Prebys Medical Discovery Institute (SBP). The photonic sensitivity of the FDSS is superior to the FlexStation; thus the assay quality control analysis for the 384-well format using the Hamamatsu 7000 calculated an improved Z' both for the CRF activation (Z'=0.89) and inhibition (Z'=0.71). Having demonstrated the robustness of the assay, we then screened the National Institute of Health's (NIH) compound library through the Molecular Libraries Probes Center Network (MLPCN) to identify small molecule modulators.

Example 3 Identification of CRFBP(10 kD)-CRF2 Modulators Using a Novel HTS of the Molecular Libraries Small Molecule Repository (MLSMR)

The MLPCN library of approximately 350,000 compounds was tested as a key component of our efforts to find modulators of the CRFBP(10 kD)-$CRF_2$ receptor complex. This library was screened against our primary CRFBP-$CRF_2$ cell-based $Ca^{2+}$ assay, simultaneously screening for agonist and antagonist hits. Both screens performed well with an average plate Z' of 0.60 and 0.59 for the agonist and antagonist screens, respectively.

During the performance of the screening campaigns, 1,568 hits with activity >50% of the CRF maximal response at a single concentration of 13.25 µM were identified in the agonist assay and 2,056 hits were identified in the antagonist assay with >50% inhibition of the CRF $EC_{80}$ at 11.78 µM. The hit lists were first filtered cheminformatically to remove pan-assay interference compounds (PAINS) and compounds that have been deemed promiscuous in our own internal screening efforts. This left 780 agonist compounds and 1,805 antagonist compounds remaining.

Following the removal of undesirable compounds from the hits, liquid samples were re-ordered from the repository and 708 agonists and 1,728 antagonist samples were received. The liquid samples were assayed in full dose-response curves (DRCs) in the respective primary assays to obtain $EC_{50}$ (agonist) and $IC_{50}$ (antagonist) potency values.

Figure 4:
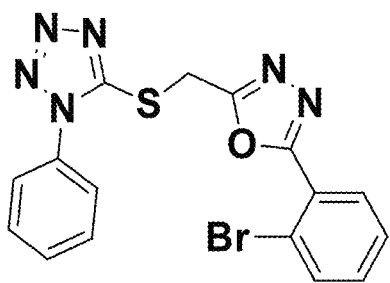
FIG. 4A-B shows CRFBP(10 kD)-CRF$_2$ antagonist hits. Compounds which fell into two series.
Figure 4:
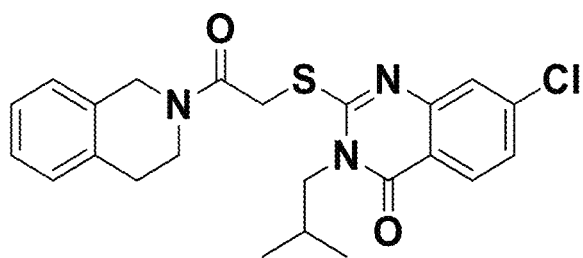
Figure 5:
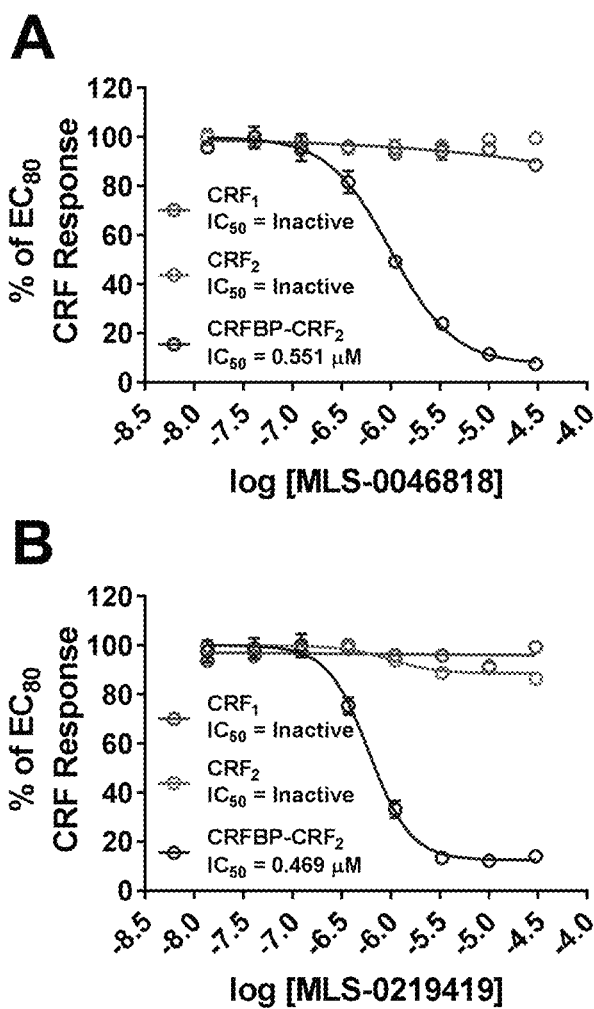
FIG. 5A-B shows that MLS-0046818 and MLS-0219419 selectively antagonize CRFBP-CRF$_2$ responses.

Chemistry and cheminformatics resources were further employed in the selection of both novel and chemically tractable molecules from the list of reconfirmed compounds. In total, 62 reconfirmed agonists and 37 reconfirmed antagonist structures were pursued through commercial vendors with additional samples acquired via analogue-by-catalogue. To eliminate compounds that may activate or inhibit $Ca^{2+}$ mobilization responses by a mechanism that is not specific to CRFBP(10 kD)-$CRF_2$ activation, these compounds were screened against HEK293 cells not expressing the CRFBP(10 kD)-$CRF_2$ receptor complex. This secondary screen eliminated all of the reconfirmed agonist hits and all but four antagonist hits. These compounds fell into two series (FIG. 4), those represented by the tetrazole-thiomethyl-oxadiazole, MLS-0046818 and those represented by the quinazolinone, MLS-0219419. These compounds were also evaluated for activity toward $CRF_2$ in the absence of CRFBP(10 kD) and for $CRF_1$ activity and were found to be inactive in these secondary assays (FIG. 5).

Example 4 Evaluation of the MOA of Novel CRFBP(10 kD)-$CRF_2$ Modulators

A Schild analysis[104] was performed in order to determine whether the antagonist lead molecules, MLS-0046818 and MLS-0219419, act at the CRFBP-$CRF_2$ complex by a competitive or noncompetitive mechanism relative to CRF. Dose-responses of CRF-induced increases in the $Ca^{2+}$ mobilization assay were performed in the absence or presence of increasing concentrations (1.11 µM, 3.33 µM, 10 µM) of either MLS-0046818 (FIG. 6A) of MLS-0219419 (FIG. 6B) in our primary CRFBP-$CRF_2$ $Ca^{2+}$ assay.

The maximum response to CRF was significantly decreased by increasing concentrations of both lead compounds. These data are consistent with a noncompetitive interaction of MLS-0046181 and MLS-0219419 with the orthosteric (endogenous) CRF site. Together with the lack of antagonist activity of these compounds toward $CRF_2$ in the absence of CRFBP (see FIG. 5), these compounds appear to act as negative allosteric modulators (NAMs) of the CRFBP-$CRF_2$ complex.

Example 5 Initial In Vitro Absorption, Distribution, Metabolism, and Excretion (ADME) and In Vivo Pharmacokinetic (PK) Characterization of Analogues MLS-0046818 and MLS-0219419 were profiled in vitro in ADME assays to assess their drug-like properties and potential for systemic activity in rodent models of alcohol use.

Our initial plasma and microsomal stability data demonstrate that while MLS-0046818 and MLS-0219419 are stable in plasma (98.6% and 71.5% remaining at 1 hour respectively), they are rapidly metabolized in both rat (0.5% and 0.1% remaining at 1 hour respectively) and human (6.6% and 0.1% remaining at 1 hour respectively) liver microsomes, performed as previously described.[105]

Both compounds were then profiled for their plasma protein binding (PPB) and brain homogenate binding (BHB) to predict the unbound drug fraction in the plasma and brain respectively. PPB and BHB were measured by equilibrium dialysis utilizing rat plasma and rat brain homogenate, as previously described.[106] While MLS-0219419 was highly bound to both plasma (0.1% free) and brain (0.0% free), MLS-0046818 displayed a higher unbound drug fraction in both plasma (4.6% free) and brain (2.3% free), indicating that this series may be more favorable for achieving target exposure.

Compounds were also evaluated for inhibition of cytochrome P450 (CYP450) enzymes using a fluorescence-based approach in insect microsomes to evaluate potential drug-drug interaction liabilities. MLS-0219419 and MLS-0046818 were also tested for inhibition of the human Ether-à-go-go-Related Gene (hERG) potassium channel binding using a competition binding assay with a tracer at Reaction Biology (Malvern, Pa.). When tested at 10 µM, MLS-0046818 and MLS-0219419 each displayed significant inhibition of CYP3A4 (91% and 76% inhibition respectively), CYP2C9 (86% and 102% inhibition respectively), and moderate inhibition of CYP1A2 (46% and 65% inhibition respectively). Alternatively, while MLS-0219419 showed no significant CYP2D6 inhibition (−21%), MLS-0046818 demonstrated the potential for CYP2D6 induction (−128% inhibition). Both compounds also demonstrated low to moderate hERG channel binding inhibition when tested at 10 µM (48% for MLS-0046818 and 86% for MLS-0219419).

Finally, MLS-0046818 and MLS-0219419 were profiled in binding assays against a comprehensive panel of CNS receptors through the NIMH Psychoactive Drug Screening Program (PDSP). For experimental details, refer to the PDSP web site.[107] Compounds were tested in quadruplicate at 10 µM final concentration using the cloned targets listed in Table 2.

As shown in Table 2, overall neither MLS-0046818 nor MLS-0219419 exhibited significant activity against the majority of the targets. MLS-0046818 exhibited >50% activity at $5HT_{2B}$ (67%) and KOR (85%) receptors.

Figure 7:
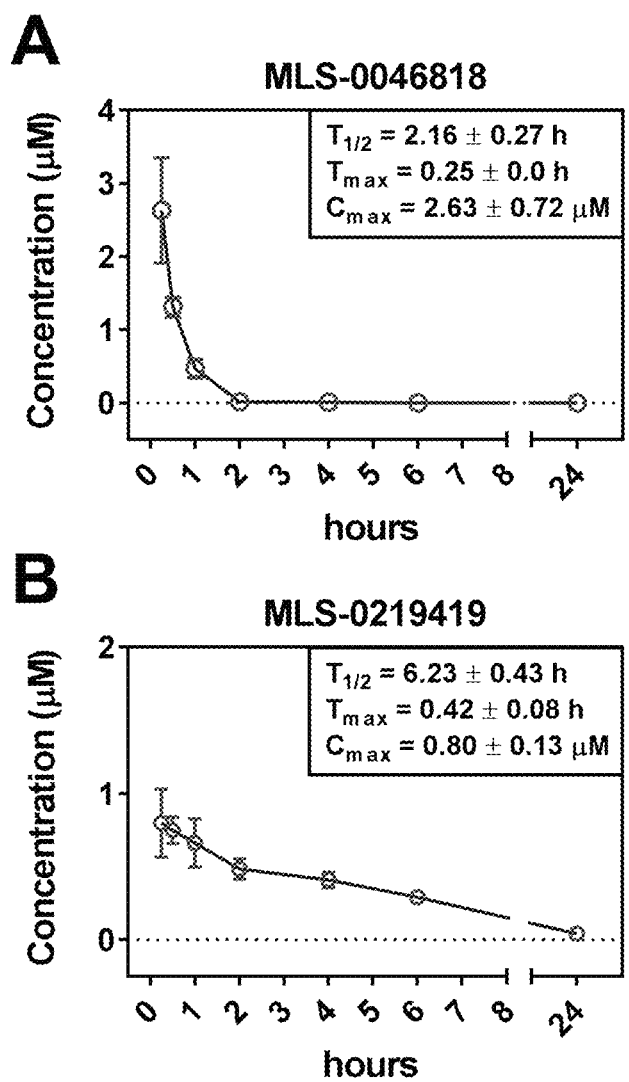

Next, plasma drug levels were determined after intraperitoneal (i.p.) dosing in mice in order to evaluate plasma and brain exposure of MLS-0046818 and MLS-0219419 (FIG. 7). Both compounds achieved high nanomolar to low micromolar plasma levels and were nearly completely eliminated after 24 hours. Comparing the plasma $C_{max}$ exposure values to the in vitro $IC_{50}$ values, MLS-0046818 achieved 4.8× its in vitro $IC_{50}$, while MLS-0219419 achieved 1.7× its in vitro $IC_{50}$.

TABLE 2

| Binding Assays Against a Panel of CNS Receptors | | |
|---|---|---|
| Receptor | MLS-0046818 | MLS-0219419 |
| 5-HT1A | 26 | −9 |
| 5-HT1B | 5 | 18 |
| 5-HT1D | −5 | −5 |
| 5-HT1E | 16 | 11 |
| 5-HT2A | 5 | −1 |
| 5-HT2B | 67 | 2 |
| 5-HT2C | 19 | −7 |
| 5-HT3 | −2 | 2 |

TABLE 2-continued

Binding Assays Against a Panel of CNS Receptors

| Receptor | MLS-0046818 | MLS-0219419 |
|---|---|---|
| 5-HT5A | −1 | 12 |
| 5-HT6 | 35 | 2 |
| 5-HT7 | −31 | 6 |
| D1 | −1 | 1 |
| D2 | −13 | −5 |
| D3 | −11 | −6 |
| D4 | −42 | −60 |
| D5 | 12 | −15 |
| SERT | −14 | −14 |
| NET | 8 | 12 |
| MOR | 12 | −4 |
| DOR | −7 | −8 |
| KOR | 85 | −10 |
| GABAA | 15 | 9 |
| H2 | 22 | 20 |
| H3 | −15 | −9 |
| H4 | 8 | −15 |
| Alpha1A | 10 | −15 |
| Alpha1B | 19 | −1 |
| Alpha2A | 4 | 8 |
| Alpha2B | 2 | 0 |
| Alpha2C | 8 | −5 |
| Beta1 | 7 | 1 |
| Beta2 | 1 | −13 |
| M1 | −15 | −15 |
| M2 | 10 | 23 |
| M3 | 13 | 19 |
| M4 | −12 | −6 |
| M5 | −6 | −2 |
| Beta3 | 27 | 29 |
| BZP Rat Brain Site | 35 | 25 |
| Alpha1D | −10 | −19 |
| Sigma 2 | −7 | 9 |
| Sigma 1 | 8 | 7 |

Samples from brains at 4 hour, 6 hour, and 24 hour post-dose were also analyzed to provide an initial estimate of brain levels. MLS-0046818 had a brain exposure of 56 nM ($0.10 \times IC_{50}$) at 4 hour post-dose, 78 nM ($0.14 \times IC_{50}$) at 6 hour post-dose, and 40 nM ($0.07 \times IC_{50}$) at 24 h post-dose. Alternatively, MLS-0219419 had a brain exposure of 245 nM ($0.52 \times IC_{50}$) at 4 hour post-dose, 764 nM ($1.63 \times IC_{50}$) at 6 hour post-dose, and 78 nM ($0.17 \times IC_{50}$) at 24 hour post-dose.

Figure 9:
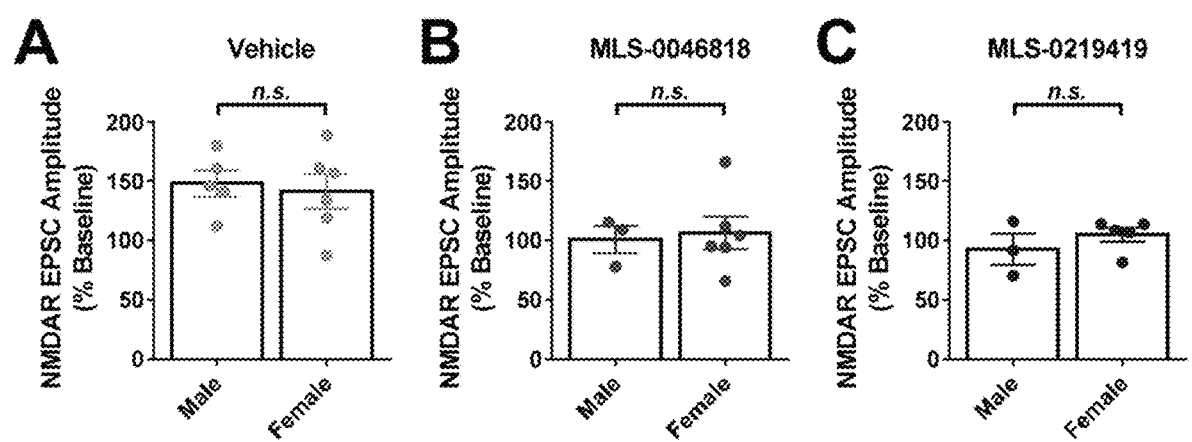

Example 6 Evaluation of the Effects of CRFBP-CRF$_2$ Modulators on CRF-Mediated NMDAR Potentiation in Ventral Tegmental Area-Dopamine Neurons NMDAR excitatory postsynaptic currents (EPSCs) were recorded from VTA dopamine (DA) neurons in acute brain slices from male and female mice. A CRF dose (1 μM), known to potentiate NMDAR responses, was washed onto the slices. As we have observed previously,[108,109] CRF potentiated NMDA receptor EPSCs recorded from VTA-DA neurons (FIG. 8A) and there was no difference in NMDAR EPSCs between male and female mice (FIG. 9).

Next, the ability of each of the two CFRBP-CRF$_2$ NAMs to block this CRF potentiation of NMDAR EPSCs was evaluated. As shown in FIG. 8B and FIG. 8C, 30 μM of MLS-0046818 or MLS-0219419 were sufficient to block the CRF effect. Again, no difference in response between male and female mice (FIG. 9). The summary of these data is presented in FIG. 8D.

Discussion

We have previously investigated the role of the full length CRFBP(37 kD) and its two fragments CRFBP(27 kD) and CRFBP(10 kD) on the signal transduction of CRF$_1$ and CRF$_2$ receptors in vitro by establishing cell lines in which these various CRFBP constructs are tethered to either CRF$_1$ and CRF$_2$. In these studies, we established that the CRFBP (10 kD) fragment tethered to CRF$_2$ results in increased Ca$^{2+}$ signaling from the CRF$_2$ receptor relative to the non-tethered CRF$_2$. However, the equivalent CRFBP(10 kD)-CRF$_1$ receptor complex and CRF$_1$ or CRF$_2$ complexes with either the full length CRFBP(37 kD) or CRFBP(27 kD) fragment do not show increases in Ca$^{2+}$ signaling relative to their non-tethered counterparts.[110] While the CRFBP(10 kD)-CRF$_2$ chimera did not represent the natural biological action in vivo, it provided the first in vitro step to investigate the association of CRF with the complex, CRFBP(10 kD)/CRF$_2$, and its role in modulating endocrine activation.[111,112] Furthermore, this in vitro chimeric tool appears to behave in a similar manner to the non-chimeric CRF$_2$, since we have previously demonstrated that the entire construct, FLAG-CRFBP(10 kD)-HA-CRF$_2$, was capable of internalization after CRF stimulation.[113,114]

To further characterize the chimeric receptor complex, we showed that CRF produced a dose-dependent stimulation of [$^{35}$S]GTPγS-binding in cell membranes expressing the FLAG-CRFBP(10 kD)-HA-CRF$_2$ chimera and this stimulation was inhibited by a CRF$_2$ antagonist. The cell-based assay was miniaturized to perform in a 384-well format without signal degradation and the screening assay was validated using LOPAC in a pilot screen. The assay was then transferred to a Hamamatsu FDSS 7000 with an improved signal response at the SBP robotic facility. This set of experiments demonstrated the robustness of the assay and suitability for screening the MLPCN library to identify small molecule modulators. It obviated the need to make and purify CRFBP to facilitate the development of a simple fluorescence calcium assay amenable to HTS.

Cell-based HTS assays have been primarily based on ligand-receptor interactions.[115] This design has been successful in the drug discovery process due to the specificity and high affinity of natural ligands to their correspondent receptor in the same system. However, the in vivo biological system interactions at receptor level are not limited to a one-to-one interaction (ligand-receptor), but they result from multiple component interactions including those with soluble binding proteins. Most proteins function in a physiological environment under crowded conditions. The approach described herein allowed us to create an in vitro environment in which proteins are expressed in a cell-like, dense state. This innovation forms the basis and the development of an HTS assay that has identified novel small molecule allosteric modulators of the CRFBP-CRF$_2$ receptor complex.

Finally, the effect of our novel small molecule allosteric modulators on electrophysiological recordings in brain slices provides validation of their neuroactive properties in a physiologically relevant system. Previous studies have demonstrated that VTA NMDAR EPSCs are potentiated by CRF through an interaction with CRFBP and CRF$_2$.[116] The current study demonstrates that this effect of CRF on NMDAR-mediated EPSCs in the VTA can be blocked through allosteric inhibition of the CRFBP complex with CRF$_2$. This is supported by the observation that a selective concentration of each of two NAMs (30 μM) inhibited the strong response to CRF (1 μM) in the VTA. Further, the results described herein support a permissive role for CRFBP where it facilitates the binding of CRF to the CRF$_2$. When CRF binds to the CRFBP, it forms a stable dimer, and undergoes conformational modifications.[171] It is possible that the compounds of the present invention might interfere with conformational changes that allow CRF to signal when bound to $CRF_2$.

It is often important for pharmacotherapies to modulate CNS receptor signaling rather than completely inhibiting the receptor, as this more closely mirrors native temporal neuronal signaling.[118] As therapeutic approach for the treatment of AUD, the embodiments of the present invention provide allosteric modulators that act on the stress system.

References

[1] HHS. Center for Behavioral Health Statistics and Quality. Key substance use and mental health indicators in the United States: Results from the 2015 National Survey on Drug Use and Health. HHS Publication No. SMA 16-4984, NSDUH Series H-5; 2016.

[2] CDC. Centers for Disease Control and Prevention, Alcohol and Public Health: Alcohol-Related Disease Impact (ARDI). 2006-2010.

[3] Goh E T, Morgan M Y. Review article: pharmacotherapy for alcohol dependence—the why, the what and the wherefore. Alimentary pharmacology & therapeutics. 2017; 45(7):865-82.

[4] Haass-Koffler C L, Akhlaghi F, Swift R M, Leggio L. Altering ethanol pharmacokinetics to treat alcohol use disorder: Can you teach an old dog new tricks? J Psychopharmacol. 2017:269881116684338.

[5] Jonas D E, Amick H R, Feltner C, Bobashev G, Thomas K, Wines R, et al. Pharmacotherapy for adults with alcohol use disorders in outpatient settings: a systematic review and meta-analysis. JAMA. 2014; 311(18):1889-900.

[6] Srisurapanont M, Jarusuraisin N. Opioid antagonists for alcohol dependence. The Cochrane database of systematic reviews. 2002(2):CD001867.

[7] Donoghue K, Elzerbi C, Saunders R, Whittington C, Pilling S, Drummond C. The efficacy of acamprosate and naltrexone in the treatment of alcohol dependence, Europe versus the rest of the world: a meta-analysis. Addiction. 2015; 110(6):920-30.

[8] Garbutt J C. Efficacy and tolerability of naltrexone in the management of alcohol dependence. Current pharmaceutical design. 2010; 16(19):2091-7.

[9] al Qatari M, Bouchenafa O, Littleton J. Mechanism of action of acamprosate. Part II. Ethanol dependence modifies effects of acamprosate on NMDA receptor binding in membranes from rat cerebral cortex. Alcoholism, clinical and experimental research. 1998; 22(4):810-4.

[10] Plosker G L. Acamprosate: A Review of Its Use in Alcohol Dependence. Drugs. 2015; 75(11):1255-68.

[11] Isselbacher et al. (1996) Harrison's Principles of Internal Medicine, 13 ed., 1814-1882.

[12] The Merck Manual of Diagnosis and Therapy, 19th Edition, published by Merck Sharp & Dohme Corp., 2011 (ISBN 978-0-911910-19-3).

[13] The Encyclopedia of Molecular Cell Biology and Molecular Medicine, Robert S. Porter et al. (eds.), published by Blackwell Science Ltd., 1999-2012 (ISBN 9783527600908).

[14] Molecular Biology and Biotechnology: a Comprehensive Desk Reference, Robert A. Meyers (ed.), published by VCH Publishers, Inc., 1995 (ISBN 1-56081-569-8).

[15] Immunology by Werner Luttmann, published by Elsevier, 2006.

[16] Janeway's Immunobiology, Kenneth Murphy, Allan Mowat, Casey Weaver (eds.), Taylor & Francis Limited, 2014 (ISBN 0815345305, 9780815345305).

[17] Lewin's Genes XI, published by Jones & Bartlett Publishers, 2014 (ISBN-1449659055).

[18] Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414).

[19] Davis et al., Basic Methods in Molecular Biology, Elsevier Science Publishing, Inc., New York, USA (2012) (ISBN 044460149X).

[20] Laboratory Methods in Enzymology: DNA, Jon Lorsch (ed.) Elsevier, 2013 (ISBN 0124199542).

[21] Current Protocols in Molecular Biology (CPMB), Frederick M. Ausubel (ed.), John Wiley and Sons, 2014 (ISBN 047150338X, 9780471503385).

[22] Current Protocols in Protein Science (CPPS), John E. Coligan (ed.), John Wiley and Sons, Inc., 2005.

[23] Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737).

[24] Koob G F, Buck C L, Cohen A, Edwards S, Park P E, Schlosburg J E, et al. Addiction as a stress surfeit disorder. Neuropharmacology. 2014; 76 Pt B:370-82.

[25] Id.

[26] HHS. Center for Behavioral Health Statistics and Quality. Key substance use and mental health indicators in the United States: Results from the 2015 National Survey on Drug Use and Health. HHS Publication No. SMA 16-4984, NSDUH Series H-5; 2016.

[27] CDC. Centers for Disease Control and Prevention, Alcohol and Public Health: Alcohol-Related Disease Impact (ARDI). 2006-2010.

[28] Goh E T, Morgan M Y. Review article: pharmacotherapy for alcohol dependence—the why, the what and the wherefore. Alimentary pharmacology & therapeutics. 2017; 45(7):865-82.

[29] Haass-Koffler C L, Akhlaghi F, Swift R M, Leggio L. Altering ethanol pharmacokinetics to treat alcohol use disorder: Can you teach an old dog new tricks? J Psychopharmacol. 2017:269881116684338.

[30] Jonas D E, Amick H R, Feltner C, Bobashev G, Thomas K, Wines R, et al. Pharmacotherapy for adults with alcohol use disorders in outpatient settings: a systematic review and meta-analysis. JAMA. 2014; 311(18):1889-900.

[31] Srisurapanont M, Jarusuraisin N. Opioid antagonists for alcohol dependence. The Cochrane database of systematic reviews. 2002(2):CD001867.

[32] Goh E T, Morgan M Y. Review article: pharmacotherapy for alcohol dependence—the why, the what and the wherefore. Alimentary pharmacology & therapeutics. 2017; 45(7):865-82.

[33] Donoghue K, Elzerbi C, Saunders R, Whittington C, Pilling S, Drummond C. The efficacy of acamprosate and naltrexone in the treatment of alcohol dependence, Europe versus the rest of the world: a meta-analysis. Addiction. 2015; 110(6):920-30.

[34] Garbutt J C. Efficacy and tolerability of naltrexone in the management of alcohol dependence. Current pharmaceutical design. 2010; 16(19):2091-7.

[35] al Qatari M, Bouchenafa O, Littleton J. Mechanism of action of acamprosate. Part II. Ethanol dependence modifies effects of acamprosate on NMDA receptor binding in membranes from rat cerebral cortex. Alcoholism, clinical and experimental research. 1998; 22(4):810-4.

[36] Plosker G L. Acamprosate: A Review of Its Use in Alcohol Dependence. Drugs. 2015; 75(11):1255-68. doi: 10.1007/s40265-015-0423-9.

[37] Goh E T, Morgan M Y. Review article: pharmacotherapy for alcohol dependence—the why, the what and the wherefore. Alimentary pharmacology & therapeutics. 2017; 45(7):865-82.

[38] Higley A E, Koob G F, Mason B J. Treatment of alcohol dependence with drug antagonists of the stress response. Alcohol Res. 2012; 34(4):516-21.

[39] Lejoyeux M, Solomon J, Ades J. Benzodiazepine treatment for alcohol-dependent patients. Alcohol and alcoholism. 1998; 33(6):563-75.

[40] Addolorato G, Leggio L, Abenavoli L, Agabio R, Caputo F, Capristo E, et al. Baclofen in the treatment of alcohol withdrawal syndrome: a comparative study vs diazepam. Am J Med. 2006; 119(3):276 e13-8.

[41] Leggio L, Kenna G A, Swift R M. New developments for the pharmacological treatment of alcohol withdrawal syndrome. A focus on non-benzodiazepine GABAergic medications. Prog Neuropsychopharmacol Biol Psychiatry. 2008; 32(5):1106-17.

[42] Haass-Koffler C L, Leggio L, Kenna G A. Pharmacological approaches to reducing craving in patients with alcohol use disorders. CNS Drugs. 2014; 28(4):343-60.

[43] Gehlert D R, Cramer J, Morin S M. Effects of corticotropin-releasing factor 1 receptor antagonism on the hypothalamic-pituitary-adrenal axis of rodents. The Journal of pharmacology and experimental therapeutics. 2012; 341(3):672-80.

[44] Spierling S R, Zorrilla E P. Don't stress about CRF: assessing the translational failures of CRF1antagonists. Psychopharmacology (Berl). 2017; 234(9-10):1467-81.

[45] Gehlert D R, Cippitelli A, Thorsell A, Le A D, Hipskind P A, Hamdouchi C, et al. 3-(4-Chloro-2-morpholin-4-yl-thiazol-5-yl)-8-(1-ethylpropyl)-2,6-dimethyl-imidazo[1,2-b]pyridazine: a novel brain-penetrant, orally available corticotropin-releasing factor receptor 1 antagonist with efficacy in animal models of alcoholism. The Journal of neuroscience: the official journal of the Society for Neuroscience. 2007; 27(10):2718-26.

[46] Haass-Koffler C L, Bartlett S E. Stress and addiction: contribution of the corticotropin releasing factor (CRF) system in neuroplasticity. Frontiers in molecular neuroscience. 2012; 5:91.

[47] Potter E, Behan D P, Linton E A, Lowry P J, Sawchenko P E, Vale W W. The central distribution of a corticotropin-releasing factor (CRF)-binding protein predicts multiple sites and modes of interaction with CRF. Proceedings of the National Academy of Sciences of the United States of America. 1992; 89(9):4192-6.

[48] Slater P G, Noches V, Gysling K. Corticotropin-releasing factor type-2 receptor and corticotropin-releasing factor-binding protein coexist in rat ventral tegmental area nerve terminals originated in the lateral hypothalamic area. The European journal of neuroscience. 2016; 43(2):220-9.

[49] Hodge C W, Haraguchi M, Erickson H, Samson H H. Ventral tegmental microinjections of quinpirole decrease ethanol and sucrose-reinforced responding. Alcoholism, clinical and experimental research. 1993; 17(2):370-5.

[50] Nowak K L, McBride W J, Lumeng L, Li T K, Murphy J M. Involvement of dopamine D2 autoreceptors in the ventral tegmental area on alcohol and saccharin intake of the alcohol-preferring P rat. Alcoholism, clinical and experimental research. 2000; 24(4):476-83.

[51] Bechtholt A J, Cunningham C L. Ethanol-induced conditioned place preference is expressed through a ventral tegmental area dependent mechanism. Behavioral neuroscience. 2005; 119(1):213-23.

[52] Brodie M S, Shefner S A, Dunwiddie T V. Ethanol increases the firing rate of dopamine neurons of the rat ventral tegmental area in vitro. Brain research. 1990; 508(1):65-9.

[53] Rodd Z A, Melendez R I, Bell R L, Kuc K A, Zhang Y, Murphy J M, et al. Intracranial self-administration of ethanol within the ventral tegmental area of male Wistar rats: evidence for involvement of dopamine neurons. The Journal of neuroscience: the official journal of the Society for Neuroscience. 2004; 24(5):1050-7.

[54] Gatto G J, McBride W J, Murphy J M, Lumeng L, Li T K. Ethanol self-infusion into the ventral tegmental area by alcohol-preferring rats. Alcohol. 1994; 11(6):557-64.

[55] Zellner M R, Kest K, Ranaldi R. NMDA receptor antagonism in the ventral tegmental area impairs acquisition of reward-related learning. Behavioural brain research. 2009; 197(2):442-9.

[56] Pignatelli M, Umanah G K, Ribeiro S P, Chen R, Karup-pagounder S S, Yau H J, et al. Synaptic Plasticity onto Dopamine Neurons Shapes Fear Learning. Neuron. 2017; 93(2):425-40.

[57] Sombers L A, Beyene M, Carelli R M, Wightman R M. Synaptic overflow of dopamine in the nucleus accumbens arises from neuronal activity in the ventral tegmental area. The Journal of neuroscience: the official journal of the Society for Neuroscience. 2009; 29(6):1735-42.

[58] Zweifel L S, Parker J G, Lobb C J, Rainwater A, Wall V Z, Fadok J P, et al. Disruption of NMDAR-dependent burst firing by dopamine neurons provides selective assessment of phasic dopamine-dependent behavior. Proceedings of the National Academy of Sciences of the United States of America. 2009; 106(18):7281-8.

[59] Hopf F W, Martin M, Chen B T, Bowers M S, Mohamedi M M, Bonci A. Withdrawal from intermittent ethanol exposure increases probability of burst firing in VTA neurons in vitro. Journal of neurophysiology. 2007; 98(4):2297-310.

[60] Haass-Koffler C L, Bartlett S E. Stress and addiction: contribution of the corticotropin releasing factor (CRF) system in neuroplasticity. Frontiers in molecular neuroscience. 2012; 5:91.

[61] Behan D P, De Souza E B, Lowry P J, Potter E, Sawchenko P, Vale W W. Corticotropin releasing factor (CRF) binding protein: a novel regulator of CRF and related peptides. Front Neuroendocrinol. 1995; 16(4):362-82.

[62] Wanat M J, Hopf F W, Stuber G D, Phillips P E, Bonci A. Corticotropin-releasing factor increases mouse ventral tegmental area dopamine neuron firing through a protein kinase C-dependent enhancement of lh. The Journal of physiology. 2008; 586(8):2157-70.

[63] Ungless M A, Singh V, Crowder T L, Yaka R, Ron D, Bonci A. Corticotropin-releasing factor requires CRF binding protein to potentiate NMDA receptors via CRF receptor 2 in dopamine neurons. Neuron. 2003; 39(3):401-7.

[64] Slater P G, Noches V, Gysling K. Corticotropin-releasing factor type-2 receptor and corticotropin-releasing factor-binding protein coexist in rat ventral tegmental area nerve terminals originated in the lateral hypothalamic area. The European journal of neuroscience. 2016; 43(2):220-9.

[65] Albrechet-Souza L, Hwa L S, Han X, Zhang E Y, DeBold J F, Miczek K A. Corticotropin Releasing Factor Binding Protein and CRF2 Receptors in the Ventral Tegmental Area: Modulation of Ethanol Binge Drinking in C57BL/6J Mice. Alcoholism, clinical and experimental research. 2015; 39(9):1609-18.

[66] Sparta D R, Hopf F W, Gibb S L, Cho S L, Stuber G D, Messing R O, et al. Binge ethanol-drinking potentiates corticotropin releasing factor R1 receptor activity in the ventral tegmental area. Alcoholism, clinical and experimental research. 2013; 37(10):1680-7.

[67] Bernier B E, Whitaker L R, Morikawa H. Previous ethanol experience enhances synaptic plasticity of NMDA receptors in the ventral tegmental area. The Journal of neuroscience: the official journal of the Society for Neuroscience. 2011; 31(14):5205-12.

[68] Albrechet-Souza L, Hwa L S, Han X, Zhang E Y, DeBold J F, Miczek K A. Corticotropin Releasing Factor Binding Protein and CRF2 Receptors in the Ventral Tegmental Area: Modulation of Ethanol Binge Drinking in C57BL/6J Mice. Alcoholism, clinical and experimental research. 2015; 39(9):1609-18.

[69] Slater P G, Noches V, Gysling K. Corticotropin-releasing factor type-2 receptor and corticotropin-releasing factor-binding protein coexist in rat ventral tegmental area nerve terminals originated in the lateral hypothalamic area. The European journal of neuroscience. 2016; 43(2):220-9.

[70] Haass-Koffler C L, Henry A T, Melkus G, Simms J A, Naemmuddin M, Nielsen C K, et al. Defining the role of corticotropin releasing factor binding protein in alcohol consumption. Transl Psychiatry. 2016; 6(11):e953.

[71] Albrechet-Souza L, Hwa L S, Han X, Zhang E Y, DeBold J F, Miczek K A. Corticotropin Releasing Factor Binding Protein and CRF2 Receptors in the Ventral Tegmental Area: Modulation of Ethanol Binge Drinking in C57BL/6J Mice. Alcoholism, clinical and experimental research. 2015; 39(9):1609-18.

[72] Woods R J, Kemp C F, David J, Sumner I G, Lowry P J. Cleavage of recombinant human corticotropin-releasing factor (CRF)-binding protein produces a 27-kilodalton fragment capable of binding CRF. The Journal of clinical endocrinology and metabolism. 1999; 84(8):2788-94.

[73] Haass-Koffler C L, Henry A T, Melkus G, Simms J A, Naemmuddin M, Nielsen C K, et al. Defining the role of corticotropin releasing factor binding protein in alcohol consumption. Transl Psychiatry. 2016; 6(11):e953.

[74] Haass-Koffler C L. The corticotropin releasing factor binding protein: A strange case of Dr. Jekyll and Mr. Hyde in the stress system? Alcohol. 2017.

[75] Slater P G, Gutierrez-Maldonado S E, Gysling K, Lagos C F. Molecular Modeling of Structures and Interaction of Human Corticotropin-Releasing Factor (CRF) Binding Protein and CRF Type-2 Receptor. Front Endocrinol (Lausanne). 2018; 9:43.

[76] Slater P G, Cerda C A, Pereira L A, Andres M E, Gysling K. CRF binding protein facilitates the presence of CRF type 2alpha receptor on the cell surface. Proceedings of the National Academy of Sciences of the United States of America. 2016; 113(15):4075-80. Epub 2016/04/02.

[77] Haass-Koffler C L, Henry A T, Melkus G, Simms J A, Naemmuddin M, Nielsen C K, et al. Defining the role of corticotropin releasing factor binding protein in alcohol consumption. Transl Psychiatry. 2016; 6(11):e953.

[78] Slater P G, Cerda C A, Pereira L A, Andres M E, Gysling K. CRF binding protein facilitates the presence of CRF type 2alpha receptor on the cell surface. Proceedings of the National Academy of Sciences of the United States of America. 2016; 113(15):4075-80. Epub 2016/04/02.

[79] Ungless M A, Singh V, Crowder T L, Yaka R, Ron D, Bonci A. Corticotropin-releasing factor requires CRF binding protein to potentiate NMDA receptors via CRF receptor 2 in dopamine neurons. Neuron. 2003; 39(3):401-7.

[80] Albrechet-Souza L, Hwa L S, Han X, Zhang E Y, DeBold J F, Miczek K A. Corticotropin Releasing Factor Binding Protein and CRF2 Receptors in the Ventral Tegmental Area: Modulation of Ethanol Binge Drinking in C57BL/6J Mice. Alcoholism, clinical and experimental research. 2015; 39(9):1609-18.

[81] Wang B, You Z B, Rice K C, Wise R A. Stress-induced relapse to cocaine seeking: roles for the CRF(2) receptor and CRF-binding protein in the ventral tegmental area of the rat. Psychopharmacology (Berl). 2007; 193(2):283-94.

[82] Haass-Koffler C L, Henry A T, Melkus G, Simms J A, Naemmuddin M, Nielsen C K, et al. Defining the role of corticotropin releasing factor binding protein in alcohol consumption. Transl Psychiatry. 2016; 6(11):e953.

[83] Koob G F, Buck C L, Cohen A, Edwards S, Park P E, Schlosburg J E, et al. Addiction as a stress surfeit disorder. Neuropharmacology. 2014; 76 Pt B:370-82.

[84] Haass-Koffler C L, Bartlett S E. Stress and addiction: contribution of the corticotropin releasing factor (CRF) system in neuroplasticity. Frontiers in molecular neuroscience. 2012; 5:91.

[85] Potter E, Behan D P, Linton E A, Lowry P J, Sawchenko P E, Vale W W. The central distribution of a corticotropin-releasing factor (CRF)-binding protein predicts multiple sites and modes of interaction with CRF. Proceedings of the National Academy of Sciences of the United States of America. 1992; 89(9):4192-6.

[86] Slater P G, Noches V, Gysling K. Corticotropin-releasing factor type-2 receptor and corticotropin-releasing factor-binding protein coexist in rat ventral tegmental area nerve terminals originated in the lateral hypothalamic area. The European journal of neuroscience. 2016; 43(2):220-9.

[87] Slater P G, Cerda C A, Pereira L A, Andres M E, Gysling K. CRF binding protein facilitates the presence of CRF type 2alpha receptor on the cell surface. Proceedings of the National Academy of Sciences of the United States of America. 2016; 113(15):4075-80. Epub 2016/04/02.

[88] Ungless M A, Singh V, Crowder T L, Yaka R, Ron D, Bonci A. Corticotropin-releasing factor requires CRF binding protein to potentiate NMDA receptors via CRF receptor 2 in dopamine neurons. Neuron. 2003; 39(3):401-7.

[89] Albrechet-Souza L, Hwa L S, Han X, Zhang E Y, DeBold J F, Miczek K A. Corticotropin Releasing Factor Binding Protein and CRF2 Receptors in the Ventral Tegmental Area: Modulation of Ethanol Binge Drinking in C57BL/6J Mice. Alcoholism, clinical and experimental research. 2015; 39(9):1609-18.

[90] Wang B, You Z B, Rice K C, Wise R A. Stress-induced relapse to cocaine seeking: roles for the CRF(2) receptor and CRF-binding protein in the ventral tegmental area of the rat. Psychopharmacology (Berl). 2007; 193(2):283-94.

[91] Haass-Koffler C L, Henry A T, Melkus G, Simms J A, Naemmuddin M, Nielsen C K, et al. Defining the role of corticotropin releasing factor binding protein in alcohol consumption. Transl Psychiatry. 2016; 6(11):e953.

[92] Woods R J, Kemp C F, David J, Sumner I G, Lowry P J. Cleavage of recombinant human corticotropin-releasing factor (CRF)-binding protein produces a 27-kilodalton fragment capable of binding CRF. The Journal of clinical endocrinology and metabolism. 1999; 84(8):2788-94.

[93] Haass-Koffler C L, Henry A T, Melkus G, Simms J A, Naemmuddin M, Nielsen C K, et al. 2016. Id.

[94] Id.

[95] Christopoulos A, Kenakin T. G protein-coupled receptor allosterism and complexing. Pharmacol Rev. 2002; 54(2): 323-74.

[96] Slater P G, Cerda C A, Pereira L A, Andres M E, Gysling K. CRF binding protein facilitates the presence of CRF type 2 alpha receptor on the cell surface. Proceedings of the National Academy of Sciences of the United States of America. 2016; 113(15):4075-80.

[97] Haass-Koffler, C. L.; Henry, A. T.; Melkus, G.; Simms, J. A.; Naemmuddin, M.; Nielsen, C. K.; Lasek, A. W.; Magill, M.; Schwandt, M. L.; Momenan, R.; Hodgkinson, C. A.; Bartlett, S. E.; Swift, R. M.; Bonci, A.; Leggio, L., Defining the role of corticotropin releasing factor binding protein in alcohol consumption. Transl Psychiatry 2016, 6 (11), e953.

[98] Id.

[99] Zhang, J. H.; Chung, T. D.; Oldenburg, K. R., A Simple Statistical Parameter for Use in Evaluation and Validation of High Throughput Screening Assays. J Biomol Screen 1999, 4 (2), 67-73.

[100] Zhang, Y.; Huo, M.; Zhou, J.; Xie, S., PKSolver: An add-in program for pharmacokinetic and pharmacodynamic data analysis in Microsoft Excel. Comput Methods Programs Biomed 2010, 99 (3), 306-14.

[101] Haass-Koffler, C. L.; Henry, A. T.; Melkus, G.; Simms, J. A.; Naemmuddin, M.; Nielsen, C. K.; Lasek, A. W.; Magill, M.; Schwandt, M. L.; Momenan, R.; Hodgkinson, C. A.; Bartlett, S. E.; Swift, R. M.; Bonci, A.; Leggio, L., Defining the role of corticotropin releasing factor binding protein in alcohol consumption. Transl Psychiatry 2016, 6 (11), e953.

[102] Id.

[103] Zhang, J. H.; Chung, T. D.; Oldenburg, K. R., A Simple Statistical Parameter for Use in Evaluation and Validation of High Throughput Screening Assays. J Biomol Screen 1999, 4 (2), 67-73.

[104] Arunlakshana, O.; Schild, H. O., Some quantitative uses of drug antagonists. Br J Pharmacol Chemother 1959, 14 (1), 48-58.

[105] Dhanya, R. P.; Sheffler, D. J.; Dahl, R.; Davis, M.; Lee, P. S.; Yang, L.; Nickols, H. H.; Cho, H. P.; Smith, L. H.; D'Souza, M. S.; Conn, P. J.; Der-Avakian, A.; Markou, A.; Cosford, N. D., Design and synthesis of systemically active metabotropic glutamate subtype-2 and -3 (mGlu2/3) receptor positive allosteric modulators (PAMs): pharmacological characterization and assessment in a rat model of cocaine dependence. Journal of medicinal chemistry 2014, 57 (10), 4154-4172.

[106] Kalvass, J. C.; Maurer, T. S., Influence of nonspecific brain and plasma binding on CNS exposure: implications for rational drug discovery. Biopharm Drug Dispos 2002, 23 (8), 327-38.

[107] https://pdspdb.unc.edu/pdspWeb/

[108] Ungless, M. A.; Singh, V.; Crowder, T. L.; Yaka, R.; Ron, D.; Bonci, A., Corticotropin-releasing factor requires CRF binding protein to potentiate NMDA receptors via CRF receptor 2 in dopamine neurons. Neuron 2003, 39 (3), 401-407.

[109] Albrechet-Souza, L.; Hwa, L. S.; Han, X.; Zhang, E. Y.; DeBold, J. F.; Miczek, K. A., Corticotropin Releasing Factor Binding Protein and CRF2 Receptors in the Ventral Tegmental Area: Modulation of Ethanol Binge Drinking in C57BL/6J Mice. Alcoholism, clinical and experimental research 2015, 39 (9), 1609-18.

[110] Haass-Koffler, C. L.; Henry, A. T.; Melkus, G.; Simms, J. A.; Naemmuddin, M.; Nielsen, C. K.; Lasek, A. W.; Magill, M.; Schwandt, M. L.; Momenan, R.; Hodgkinson, C. A.; Bartlett, S. E.; Swift, R. M.; Bonci, A.; Leggio, L., Defining the role of corticotropin releasing factor binding protein in alcohol consumption. Transl Psychiatry 2016, 6 (11), e953.

[111] Haass-Koffler, C. L., The corticotropin releasing factor binding protein: A strange case of Dr. Jekyll and Mr. Hyde in the stress system? Alcohol 2017.

[112] Lowry, P. J.; Koerber, S. C.; Woods, R. J.; Baigent, S.; Sutton, S.; Behan, D. P.; Vale, W.; Rivier, J., Nature of ligand affinity and dimerization of corticotrophin-releasing factor-binding protein may be detected by circular dichroism. J Mol Endocrinol 1996, 16 (1), 39-44.

[113] Haass-Koffler, C. L.; Henry, A. T.; Melkus, G.; Simms, J. A.; Naemmuddin, M.; Nielsen, C. K.; Lasek, A. W.; Magill, M.; Schwandt, M. L.; Momenan, R.; Hodgkinson, C. A.; Bartlett, S. E.; Swift, R. M.; Bonci, A.; Leggio, L., Defining the role of corticotropin releasing factor binding protein in alcohol consumption. Transl Psychiatry 2016, 6 (11), e953.

[114] Haass-Koffler, C. L.; Naeemuddin, M.; Bartlett, S. E., An analytical tool that quantifies cellular morphology changes from three-dimensional fluorescence images. J Vis Exp 2012, (66), e4233.

[115] Tian, Y. E.; Wu, L. H.; Mueller, W. T.; Chung, F. Z., A Screening Strategy Based on Differential Binding of Ligand to Receptor and to Binding Proteins: Screening for Compounds Interacting with Corticotrophin-Releasing Factor-Binding Protein. J Biomol Screen 1999, 4 (6), 319-326.

[116] Ungless, M. A.; Singh, V.; Crowder, T. L.; Yaka, R.; Ron, D.; Bonci, A., Corticotropin-releasing factor requires CRF binding protein to potentiate NMDA receptors via CRF receptor 2 in dopamine neurons. Neuron 2003, 39 (3), 401-407.

[117] Lowry, P. J.; Koerber, S. C.; Woods, R. J.; Baigent, S.; Sutton, S.; Behan, D. P.; Vale, W.; Rivier, J., Nature of ligand affinity and dimerization of corticotrophin-releasing factor-binding protein may be detected by circular dichroism. J Mol Endocrinol 1996, 16 (1), 39-44.

[118] Lewis, J. A.; Lebois, E. P.; Lindsley, C. W., Allosteric modulation of kinases and GPCRs: design principles and structural diversity. Curr Opin Chem Biol 2008, 12 (3), 269-280.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain using no more than routine experimentation, many equivalents to the specific embodiments described herein. Such equivalents are intended to be encompassed by the following claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of treating alcohol use disorder comprising the step of administering to a subject, in need thereof, a composition comprising a therapeutically-effective amount of a negative allosteric modulator (NAM) of the CRFBP(10 kD)-$CRF_2$ complex, wherein the NAM is selected from a compound of the formula:

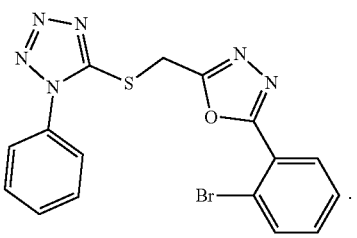 [SMILES: Brc1ccccc1-c1nnc(CSc2nnnn2-c2ccccc2)o1]

or

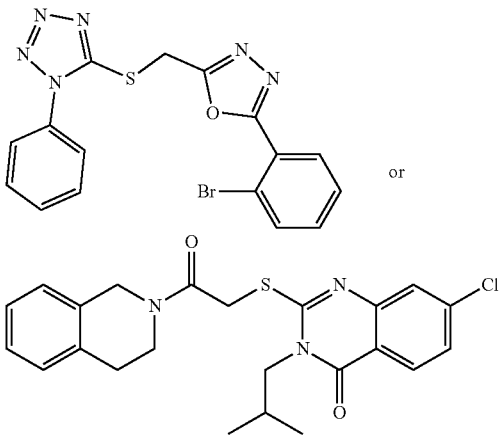

and wherein the composition downregulates CRF-induced potentiation of N-Methyl-D-aspartic acid receptor (NMDAR)-mentioned synaptic transmission in dopamine neurons in the ventral tegmental area (VTA) of the subject.

2. The method of claim 1 wherein the NAM selectively antagonizes CRF at the CRFBP-$CRF_2$ complex but lack antagonistic activity toward $CRF_2$ alone and $CRF_1$.

3. The method of claim 2 wherein the NAM is a compound of the formula:

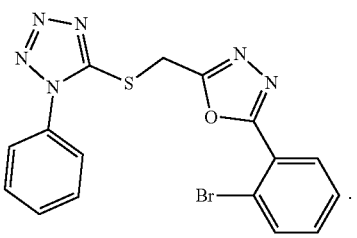 [SMILES: Brc1ccccc1-c1nnc(CSc2nnnn2-c2ccccc2)o1]

.

4. The method of claim 2 wherein the NAM is a compound of the formula:

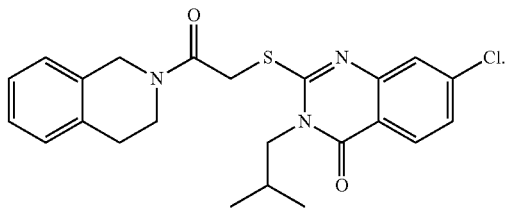 [SMILES: CC(C)Cn1c(SCC(=O)N2CCc3ccccc3C2)nc2cc(Cl)ccc2c1=O]

* * * * *

UNITED STATES PATENT AND TRADEMARK OFFICE
CERTIFICATE OF CORRECTION

| | | |
|---|---|---|
| PATENT NO. | : 11,278,527 B2 | Page 1 of 1 |
| APPLICATION NO. | : 17/273607 | |
| DATED | : March 22, 2022 | |
| INVENTOR(S) | : Carolina L. Haass-Koffler | |

It is certified that error appears in the above-identified patent and that said Letters Patent is hereby corrected as shown below:

On the Title Page

Item (12) "Haass-Koffler" should read:
--Haass-Koffler et al.--.

Item (72) Inventor should read:
--(72) Inventors: Carolina L. Haass-Koffler, Providence, RI (US)
　　　　　　　　 Douglas James Sheffler, San Diego, CA (US)
　　　　　　　　 Nicholas David Peter Cosford, San Diego, CA (US)--.

Item (73) Assignee should read:
--(73) Assignees: Brown University, Providence, RI (US)
　　　　　　　　　Sanford Burnham Prebys Medical Discovery Institute, La Jolla, CA (US)--.

Signed and Sealed this
Ninth Day of December, 2025

John A. Squires
*Director of the United States Patent and Trademark Office*